US012629104B2

(12) United States Patent
Davis et al.

(10) Patent No.: US 12,629,104 B2
(45) Date of Patent: May 19, 2026

(54) SYSTEM FOR VERIFYING A PATHOLOGIC EPISODE USING AN ACCELEROMETER

(71) Applicant: Pacesetter, Inc., Sylmar, CA (US)

(72) Inventors: Kevin J. Davis, Thousand Oaks, CA (US); Nima Badie, Oakland, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 772 days.

(21) Appl. No.: 18/057,508

(22) Filed: Nov. 21, 2022

(65) Prior Publication Data

US 2023/0263480 A1 Aug. 24, 2023

Related U.S. Application Data

(60) Provisional application No. 63/268,284, filed on Feb. 21, 2022.

(51) Int. Cl.
 A61B 5/11 (2006.01)
 A61B 5/00 (2006.01)
 G01P 15/18 (2013.01)
(52) U.S. Cl.
 CPC .......... A61B 5/7282 (2013.01); A61B 5/1118 (2013.01); A61B 5/6847 (2013.01); G01P 15/18 (2013.01); A61B 2562/0219 (2013.01)
(58) Field of Classification Search
 CPC . A61B 2562/0219; A61B 5/1118; A61B 5/36; A61B 5/6847; A61B 5/686;

(Continued)

(56) References Cited

U.S. PATENT DOCUMENTS

| 6,044,297 A | 3/2000 | Sheldon et al. |
| 6,102,874 A | 8/2000 | Stone et al. |

(Continued)

FOREIGN PATENT DOCUMENTS

| EP | 1331022 A2 | 7/2003 |
| WO | 2007111728 A2 | 10/2007 |

OTHER PUBLICATIONS

Extended European Search Report for corresponding EP Application No. 21156178.2-1122 dated Dec. 7, 2021 (9 pages).

*Primary Examiner* — George Manuel
(74) *Attorney, Agent, or Firm* — Dean D. Small; Carroll, Hoette & Butscher, LLC

(57) ABSTRACT

A system for verifying a candidate pathologic episode of a patient is provided that includes an accelerometer configured to be implanted in the patient. The accelerometer is configured to obtain accelerometer data along at least one axis. The system also includes a memory configured to store program instructions, and one or more processors that, when executing the program instructions, are configured to obtain accelerometer data. The one or more processors are also configured to determine a plurality of control three-dimensional point vectors related to the accelerometer data, and obtain a biological signal and identify a candidate pathologic episode based on the biological signal. The one or more processors are also configured to analyze the plurality of control three-dimensional point vectors to identify a physical action experienced by the patient, and verify the candidate pathologic episode based on the physical action.

25 Claims, 14 Drawing Sheets

3-D POINT PLOT

(58) Field of Classification Search
    CPC ........... A61B 5/7282; A61B 5/00; A61B 5/11;
    G01P 15/18
    See application file for complete search history.

(56)                     References Cited

U.S. PATENT DOCUMENTS

| | | | |
|---|---|---|---|
| 6,658,292 B2 | 12/2003 | Kroll et al. | |
| 6,751,503 B1 | 6/2004 | Kroll | |
| 8,005,543 B2 | 8/2011 | Libbus et al. | |
| 8,108,035 B1 | 1/2012 | Bharmi | |
| 8,308,661 B2 | 11/2012 | Miesel et al. | |
| 8,475,387 B2 | 7/2013 | Derchak et al. | |
| 8,684,922 B2 | 4/2014 | Tran | |
| 9,636,069 B2* | 5/2017 | Chakravarthy ...... | A61B 5/7264 |
| 9,642,537 B2 | 5/2017 | Felix et al. | |
| 10,124,172 B2 | 11/2018 | Lyons et al. | |
| 10,610,132 B2 | 4/2020 | Gunderson et al. | |
| 2008/0081958 A1 | 4/2008 | Denison et al. | |
| 2011/0098934 A1* | 4/2011 | Hubler ................. | A61B 5/6814 |
| | | | 702/19 |
| 2018/0132793 A1* | 5/2018 | Katra ................... | A61B 5/0002 |
| 2018/0325466 A1 | 11/2018 | An et al. | |
| 2019/0008384 A1 | 1/2019 | Brisben et al. | |
| 2023/0071085 A1* | 3/2023 | Doomra .............. | A61B 5/7264 |

* cited by examiner

TIME SERIES                                   3-D POINT PLOT

FIG. 2G                                         FIG. 2H

3-D POINT PLOT

1200

SYSTEM FOR VERIFYING A PATHOLOGIC EPISODE USING AN ACCELEROMETER

CROSS REFERENCE TO RELATED APPLICATIONS

This application relates to and claims priority benefits from U.S. Provisional Application No. 63/268,284, entitled "SYSTEM FOR VERIFYING A PATHOLOGIC EPISODE USING AN ACCELEROMETER," filed Feb. 21, 2022, which is hereby incorporated by reference in its entirety.

BACKGROUND

Embodiments herein generally relate to a method of detecting a pathologic episode by using an accelerometer implanted within a patient.

A three-dimensional (3-D) accelerometer that is implanted in a patient may detect movement of the patient during day to day activities. For example, an accelerometer may be part of an implantable cardiac monitor (ICM) or within another similar implantable medical device (IMD) to detect rotation based on the position and/or orientation of the ICM. Still, often accelerometers may be underutilized when used within an IMD.

3-D accelerometers have been previously utilized to determine if a patient is undergoing a pathologic episode, or simply performing an activity such as exercising that results in a false detection of the pathologic episode. As an example, U.S. patent application Ser. No. 17/192,961, filed Mar. 5, 2021, Titled "SYSTEM FOR VERIFYING A PATHO-LOGIC EPISODE USING AN ACCELEROMETER" that claims priority to U.S. Provisional Application No. 63/021, 778, Titled "SYSTEM FOR VERIFYING A PATHOLOGIC EPISODE USING AN ACCELEROMETER" which was filed on 8 May 2020; and also claims priority to United Stated Provisional Application No. 63/139,304, Titled "SYSTEM FOR VERIFYING A PATHOLOGIC EPISODE USING AN ACCELEROMETER" which was filed on 19 Jan. 2021, the complete subject matter of each are expressly incorporated herein by reference in their entirety. These application not only provide for the use of the 3-D acceler-ometers for verifying pathologic episodes, but also for detecting medical conditions such as a syncope. Still, the amount of energy consumed by an IMD to provide such functionality can reduce the life expectably of the IMD itself. By having to store 3-D accelerometer motion data, constantly monitor the patient using the 3-D accelerometer, etc. can cause consumption of the battery of the IMD that has a finite life.

BRIEF SUMMARY

In accordance with embodiments herein a system for verifying a candidate pathologic episode of a patient is provided that includes an accelerometer configured to be implanted in the patient. The accelerometer is configured to obtain accelerometer data along at least one axis. The system also includes a memory configured to store program instruc-tions, and one or more processors that, when executing the program instructions, are configured to obtain accelerometer data. The one or more processors are also configured to determine a plurality of control three-dimensional point vectors related to the accelerometer data, and obtain a biological signal and identify a candidate pathologic episode based on the biological signal. The one or more processors are also configured to analyze the plurality of control three-dimensional point vectors to identify a physical action experienced by the patient, and verify the candidate patho-logic episode based on the physical action.

Optionally, to determine the plurality of control three-dimensional point vectors includes analyzing the acceler-ometer data, and approximating the plurality of control three-dimensional point vectors related to the accelerometer data. In one aspect, the one or more processors are further configured to store the plurality of control three-dimensional point vectors in the memory and discard the accelerometer data. In another aspect, the one or more processors are further configured to store the candidate pathologic episode in the memory as an actual episode or a false episode based on the physical action analyzed. In one example, the one or more processors are further configured to determine if the plurality of control three-dimensional point vectors are required to make a diagnosis based on the biological signal. In another example, the physical action is activity of the patient or change in position of the patient. In yet another example, the one or more processors are further configured to deny the candidate pathologic episode as a false episode when the physical action does not correspond to the candi-date pathologic episode. In one embodiment, the biological signal corresponds to a cardiac activity signal, and the candidate pathologic episode is at least one of a heart failure, stroke, syncope, arrythmia, heart attack, brady event, asys-tole, ventricular fibrillation, ventricular tachycardia, or sei-zure. In another embodiment, responsive to identifying the candidate pathologic episode, the one or more processors are configured to obtain accelerometer data for an interval associated with the candidate pathologic episode, determine a plurality of activity three-dimensional point vectors, and compare the plurality of activity three-dimensional point vectors with the plurality of control three-dimensional point vectors. Optionally, analyzing the plurality of control three-dimensional point vectors to identify the physical action experienced by the patient includes comparing the plurality of activity three-dimensional point vectors with the plurality of control three-dimensional point vectors.

In accordance with embodiments herein, a computer implemented method is provided for verifying a candidate pathologic episode of a patient. The method includes obtain-ing accelerometer data, determining a plurality of control three-dimensional point vectors related to the accelerometer data, and obtaining a biological signal and identify a can-didate pathologic episode based on the biological signal. The method also includes analyzing the plurality of control three-dimensional point vectors to identify a physical action experienced by the patient, and verifying the candidate pathologic episode based on the physical action.

Optionally, determining the plurality of control three-dimensional point vectors includes analyzing the acceler-ometer data, and approximating the plurality of control three-dimensional point vectors related to the accelerometer data. In one aspect, the method also includes storing the plurality of control three-dimensional point vectors in the memory and discarding the accelerometer data. In another aspect, the method also includes storing the candidate patho-logic episode in the memory as an actual episode or a false episode based on the physical action analyzed. In one example, the method also includes determining if the plu-rality of control three-dimensional point vectors are required to make a diagnosis based on the biological signal.

In accordance with embodiments herein a system for verifying a candidate pathologic episode of a patient is also provided. The system includes an accelerometer configured to be implanted in the patient, the accelerometer configured to obtain accelerometer data along at least one axis. The system also includes a memory configured to store program instructions, and one or more processors that, when executing the program instructions, are configured to obtain accelerometer data. The one or more processors are also configured to determine a plurality of control three-dimensional point vectors related to the accelerometer data, and obtain a biological signal and identify a candidate pathologic episode based on the biological signal, The one or more processors are also configured to, responsive to identifying the candidate pathologic episode, obtain accelerometer data for an interval associated with the candidate pathologic episode. The one or more processors are also configured to determine a plurality of activity three-dimensional point vectors related to the interval associated with the candidate pathologic episode, compare the activity three-dimensional point vectors to the control three-dimensional point vectors, and verify the candidate pathologic episode based on the comparison between the activity three-dimensional point vectors and the control three-dimensional point vectors.

Optionally, to determine the plurality of control three-dimensional point vectors includes analyzing the accelerometer data, and approximating the plurality of control three-dimensional point vectors related to the accelerometer data. In one aspect, the one or more processors are further configured to store the plurality of control three-dimensional point vectors in the memory and discard the accelerometer data. In another aspect, the one or more processors are further configured to store the candidate pathologic episode in the memory as an actual episode or a false episode based on the comparison between the activity three-dimensional point vectors and the control three-dimensional point vectors. In one example, the one or more processors are further configured to determine if the plurality of control three-dimensional point vectors are required to make a diagnosis based on the biological signal.

BRIEF DESCRIPTION OF THE DRAWINGS

FIG. 2G illustrates a time series graph of accelerometer data in accordance with embodiments herein.

FIG. 2H illustrates a three-dimensional graph of position over time in accordance with embodiments herein.

DETAILED DESCRIPTION

Figure 1:
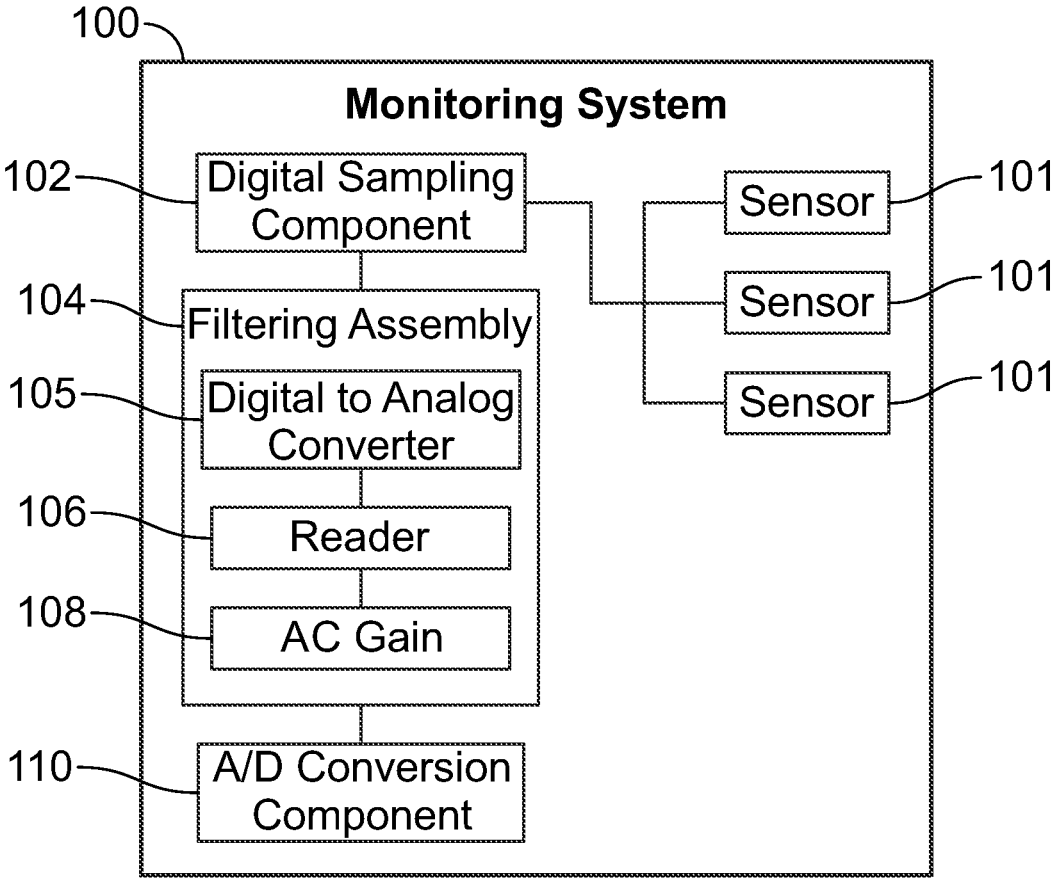
FIG. 1 illustrates a block diagram of an accelerometer formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The term "IMD" shall mean an implantable medical device. Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. application Ser. No. 15/973,195, entitled "SUBCUTANEOUS IMPLANTATION MEDICAL DEVICE WITH MULTIPLE PARASTERNAL-ANTERIOR ELECTRODES" filed May 7, 2018; U.S. application Ser. No. 15/973,219, entitled "IMPLANTABLE MEDICAL SYSTEMS AND METHODS INCLUDING PULSE GENERATORS AND LEADS" filed May 7, 2018; U.S. application Ser. No. 15/973,249, entitled "SINGLE SITE IMPLANTATION METHODS FOR MEDICAL DEVICES HAVING MULTIPLE LEADS", filed May 7, 2018, which are hereby incorporated by reference in their entireties. Further, one or more combinations of IMDs may be utilized from the above incorporated patents and applications in accordance with embodiments herein. Embodiments may be implemented in connection with one or more subcutaneous implantable medical devices (S-IMDs). For example, the S-IMD may include one or more structural and/or functional aspects of the device(s) described in U.S. application Ser. No. 15/973,219, entitled "IMPLANTABLE MEDICAL SYSTEMS AND METHODS INCLUDING PULSE GENERATORS AND LEADS", filed May 7, 2018; U.S. application Ser. No. 15/973,195, entitled "SUBCUTANEOUS IMPLANTATION MEDICAL DEVICE WITH MULTIPLE PARASTERNAL-ANTERIOR ELECTRODES", filed May 7, 2018; which are hereby incorporated by reference in their entireties. The IMD may represent a passive device that utilizes an external power source, and entirely mechanical plan will device, and/or an active device that includes an internal power source. The IMD may deliver some type of therapy/treatment, provide mechanical circulatory support, and/or merely monitor one or more physiologic characteristics of interest (e.g., PAP, CA signals, impedance, heart sounds).

Additionally or alternatively, embodiments herein may be implemented in connection with an integrated healthcare patient management system or network, such as described in "METHODS, DEVICE AND SYSTEMS FOR HOLISTIC INTEGRATED HEALTHCARE PATIENT MANAGEMENT", provisional application 62/875,870, filed Jul. 18, 2019, which is incorporated by reference herein in its entirety.

Additionally or alternatively, embodiments herein may be implemented in connection with the methods and systems described in "METHOD AND SYSTEM FOR HEART CONDITION DETECTION USING AN ACCELEROMETER", Provisional Application No. 63/021,775, which is incorporated by reference herein in its entirety.

Additionally or alternatively, embodiments herein may be implemented in connection with the methods and systems described in "METHOD AND DEVICE FOR DETECTING RESPIRATION ANOMALY FROM LOW FREQUENCY COMPONENT OF ELECTRICAL CARDIAC ACTIVITY SIGNALS", U.S. application Ser. No. 16/869,733, filed on the same day as the present application, which is incorporated by reference herein in its entirety.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the ICM and a local external device, and/or iii) receiving the data, signals, information, etc. at a remote server over a network connection. The obtaining operation, when from the perspective of an ICM, may include sensing new signals in real time, and/or accessing memory to read stored data, signals, information, etc. from memory within the ICM. The obtaining operation, when from the perspective of a local external device, includes receiving the data, signals, information, etc. at a transceiver of the local external device where the data, signals, information, etc. are communicated from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The terms "three-dimensional point vector" and "three-dimensional point vectors" shall mean any set of points that include an X-coordinate, Y-coordinate, and Z-coordinate utilized to approximate or estimate data, including accelerometer data. Each coordinate of the three-dimensional point vector can be a zero or non-zero number. The zero or non-zero number may be an integer, fraction, decimal, or the like. In one example, plural three-dimensional point vectors may be utilized to form a shape that approximates the shape of an accelerometer data set that provides numerous vectors that include X-coordinates, Y-coordinates, and Z-coordinates. As an example, the accelerometer data set may include a hundred, thousand, etc. three-dimensional vectors related to the movement of a patient over time. Each three-dimensional point vector estimates, averages, etc. the positions of the accelerometer data set to define a shape made by the hundred, thousand, etc. three-dimensional vectors with less three-dimensional point vectors. So, in one example, an individual may jog, resulting in an accelerometer data set that forms a pattern based on one hundred individual three-dimensional vectors. From the one hundred individual three-dimensional vectors, ten three-dimensional point vectors may be formed to approximate the shape formed by the one-hundred individual three-dimensional vectors. In one example, the approximation is a piecewise linear approximation. Similarly, in another example, a thousand individual three-dimensional vectors may form a patterned shape from an individual going up a set of stairs. In this example, one hundred three-dimensional point vectors may be approximated, or estimated to define the same shape. By forming three-dimensional point vectors to approximate a much larger set of three-dimensional vector data, the one or more processors may discard the accelerometer data, and memory space is saved, reducing wear on a battery. When used herein "control three-dimensional point vectors" refer to point vectors formed at a predetermined time when an activity of a patient is known. When used herein "activity three-dimensional point vectors" refers to three-dimensional point vectors determined after the predetermined time when the activity of the patient is unknown. When the activity of the patient is unknown, the activity three-dimensional point vectors may be compared to the control three-dimensional point vectors to determine the activity of the patient.

FIG. 1 illustrates a schematic diagram of a monitoring system 100. In one example, the monitoring system is or includes an accelerometer. In one embodiment when the monitoring system 100 is an accelerometer, the accelerometer may be a chip for placement in an IMD. In another embodiment, the accelerometer is formed and operates in the manner described in U.S. Pat. No. 6,937,900, titled "AC/DC Multi-Axis Accelerometer For Determining A Patient Activity And Body Position," the complete subject matter which is expressly incorporated herein by reference. In an embodiment, when the monitoring system is an accelerometer, the accelerometer includes sensors that generate first (X), second (Y) and third (Z) accelerometer signals along corresponding X, Y and Z axes (also referred to as first axis accelerometer signals, second axis accelerometer signals and third axis accelerometer signals). The X, Y and Z axes accelerometer signals collectively define a three-dimensional (3D), or multi-dimensional (MD) accelerometer data set. While examples herein are described in connection with an accelerometer that generates accelerometer signals along three orthogonal axes, it is recognized that embodiments may be implemented wherein accelerometer signals are generated along two or more axes, including more than three axes. The accelerometer signals in one example are utilized to determine three-dimensional vectors. The three-dimensional vectors can be used to estimate, predict, determine three-dimensional point vectors.

The monitoring system 100 may include sensors 101 that monitor and receive signals from the X, Y and Z axes. In one embodiment, the individual X, Y and Z signals are received by a digital sampling component 102 that receives a digital input. Coupled to the digital sampling component 102 is a filtering assembly 104 that may include a digital to analog converter 105 to form an alternating current (AC) signal, a reader device 106, and an AC gain device 108. While in this embodiment, the filtering assembly includes the devices provided, in other examples, other devices may be utilized to filter the digital input signal for processing.

The monitoring system 100 may also include an analog to digital conversion component 110, along with a position, or direct current (DC) component. In one example, the analog to digital conversion component may be an 8-bit analog to digital converter (ADC). The evaluation version of the monitoring system 100 may provide 3-axis (X and Y along the chip, Z normal to the chip) DC-coupled posture signal corresponding to 3 orthogonal directions as well as 3-axis AC-coupled activity signal. In one embodiment, each of the 6 signal may be sampled at 100 Hz and accumulated over 1 sec for a total of 12 signals([X/Y/Z],[posture/activity], [100/1 Hz]). This MD accelerometer data may be used to describe embodiments herein.

While described as a digital signal in relation to FIG. 1, in other embodiments the signal may be an analog signal, filtered, amplified, etc. The accelerometer data signals may be recorded in a data storage of the accelerometer, of an IMD, of a remote device etc. Alternatively, the accelerometer data set may be collected from a remote device, or received from a storage device coupled to the accelerometer. To this end, the accelerometer data set may be a multi-dimensional accelerometer data set.

The accelerometer sensors 101 may collect accelerometer signals from two or more axes. The accelerometer signals may come from at least two of the X-axis, Y-axis, or Z-axis. In one example, the accelerometer signals may be collected from all three axes.

FIGS. 2A-2F illustrate example accelerometer signals that may be collected and recorded over 1 second intervals by the monitoring system 100 of FIG. 1. Specifically, IMD accelerometer signals may be collected and recorded, including both posture related data sets and activity related data sets. Posture related data sets include the positions and changes in position of the patient along an X axis, Y axis, and/or Z axis. Activity related data sets include measurements related to the activity of the patient, including walking, running, sleeping, sitting up, jogging, falling, or the like.

The posture related data sets and activity related data sets may be obtained at any time. In one example, the posture related data sets and activity related data sets are control accelerometer data sets that are obtained at a first time when a patient performs the posture or activity to provide a base-line or control for comparison. Alternatively, the posture related data sets and activity related data sets can be activity accelerometer data sets that are obtained after the first time, and at a second time. The control accelerometer data sets can then be used to determine control three-dimensional point vectors, while the activity accelerometer data sets can be utilized to determine activity three-dimensional point vectors that can be compared to the control three-dimensional point vectors to determine the activity of a patient, vary treatment, or the like. While in the example at the second time activity accelerometer data sets are obtained, additional control accelerometer data sets may be obtained after the first time, including at a second time.

Figure 2A:
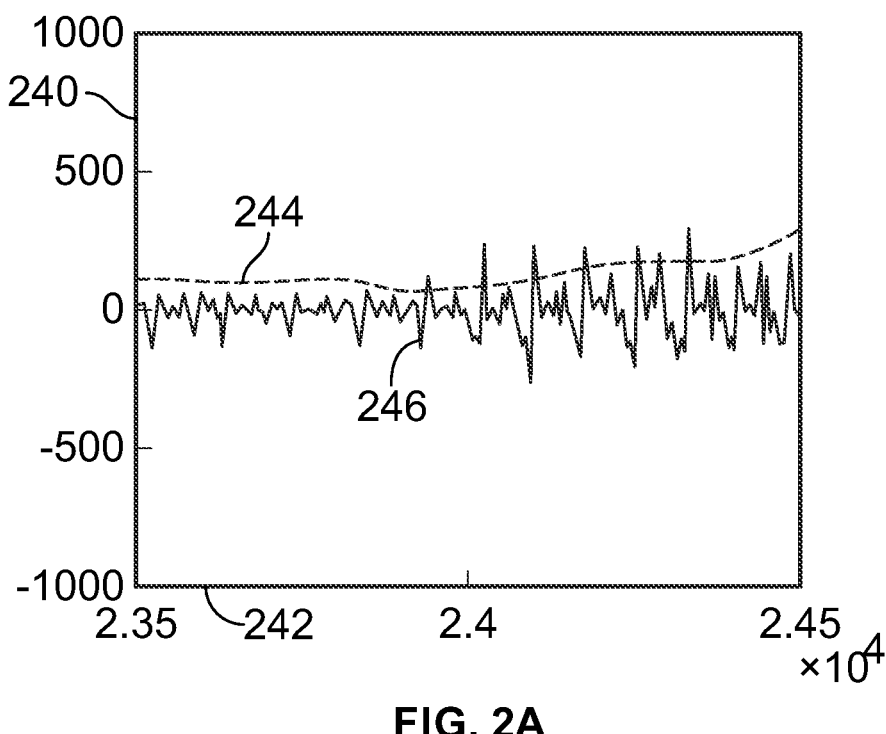
FIG. 2A illustrates a graph of activity over time in accordance with embodiments herein.
Figure 2B:
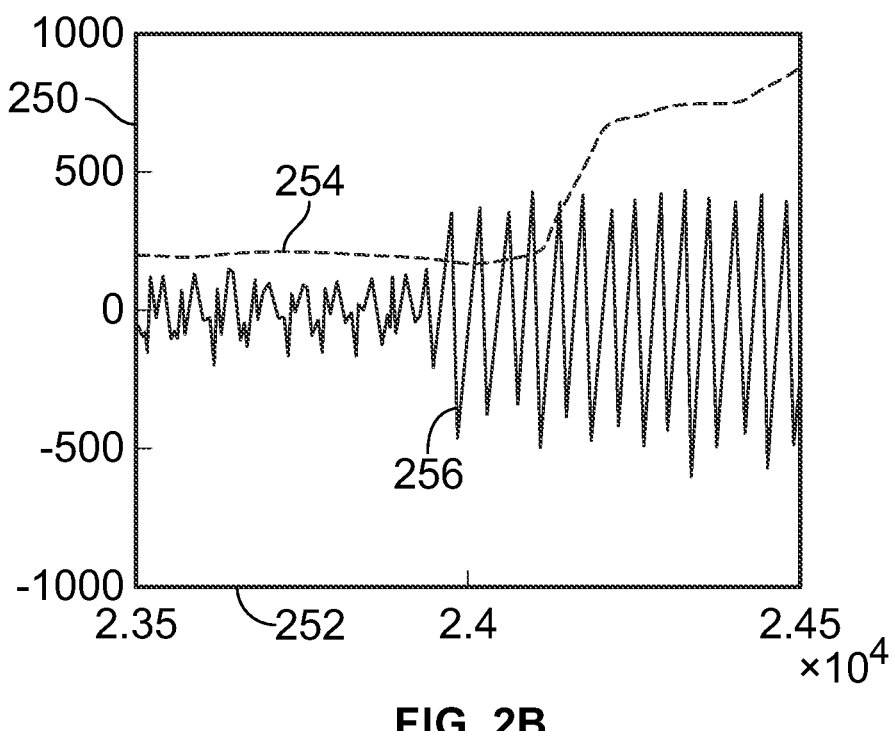
FIG. 2B illustrates a graph of activity over time in accordance with embodiments herein.
Figure 2C:
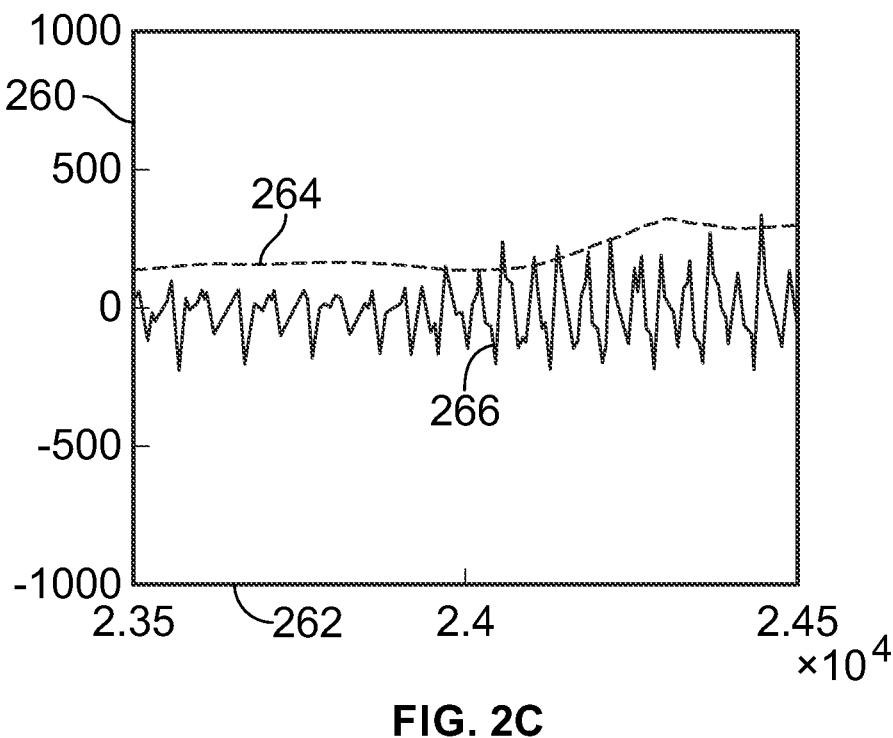
FIG. 2C illustrates a graph of activity over time in accordance with embodiments herein.

FIG. 2A illustrates an activity level of the patient 240 over time 242 for the X axis, with activity of the patient over 1 second 244 monitored, along with 100 Hz activity of the patient over 1 second 246. Similarly, FIG. 2B illustrates activity level of the patient 250 over time 252 for the Y axis, with activity over 1 second 254 monitored, along with 100 Hz activity over 1 second 256. FIG. 2C meanwhile illustrates activity level of the patient 260 over time 262 for the Z axis, with activity level of the patient over 1 second 264 monitored, along with 100 Hz activity over 1 second 266.

Figure 2D:
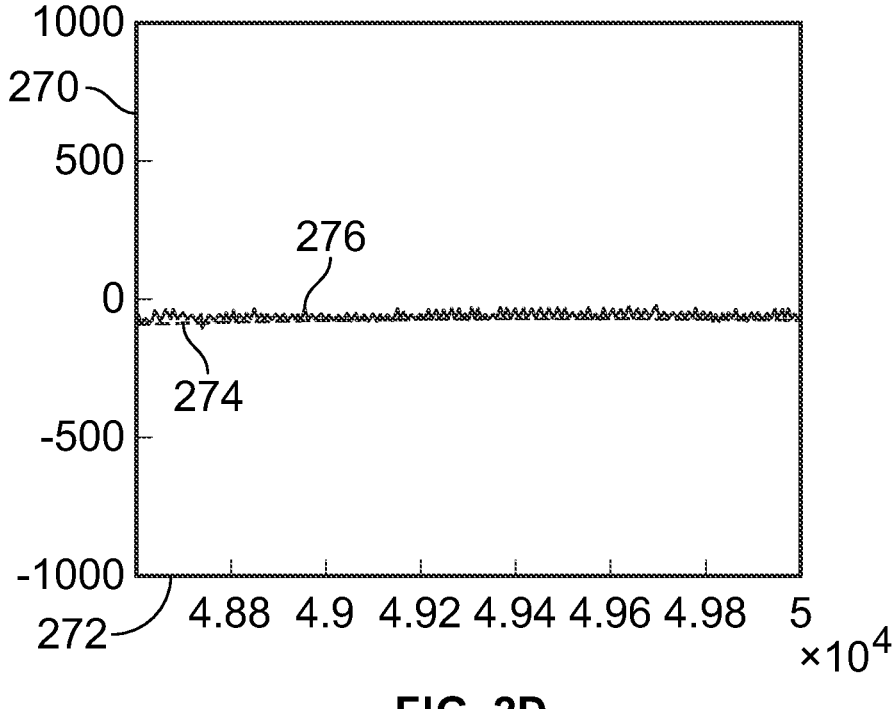
FIG. 2D illustrates a graph of position over time in accordance with embodiments herein.
Figure 2E:
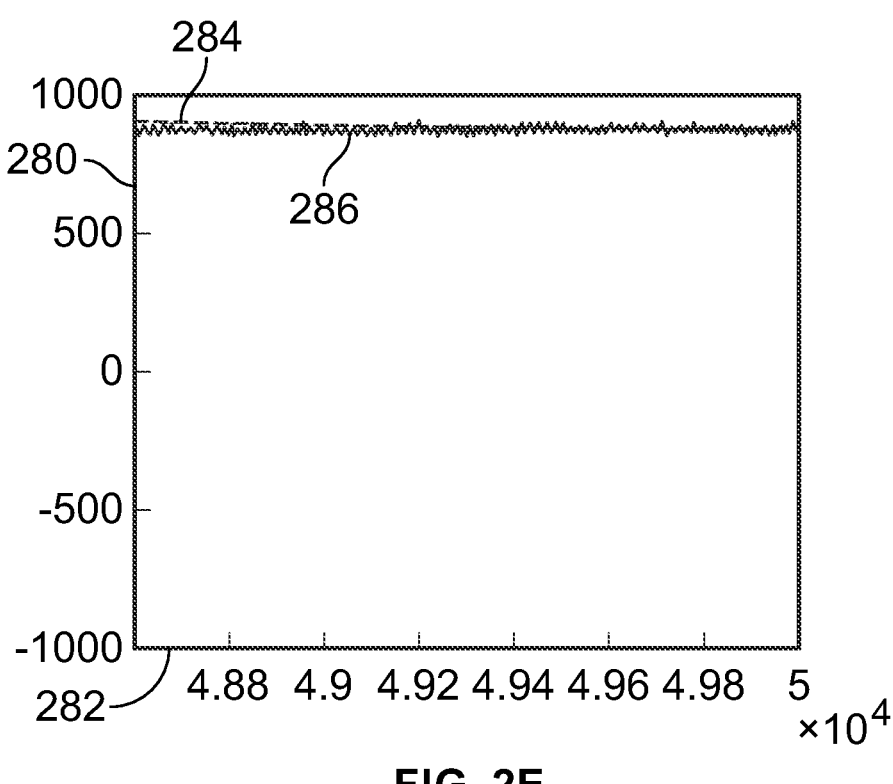
FIG. 2E illustrates a graph of position over time in accordance with embodiments herein.
Figure 2F:
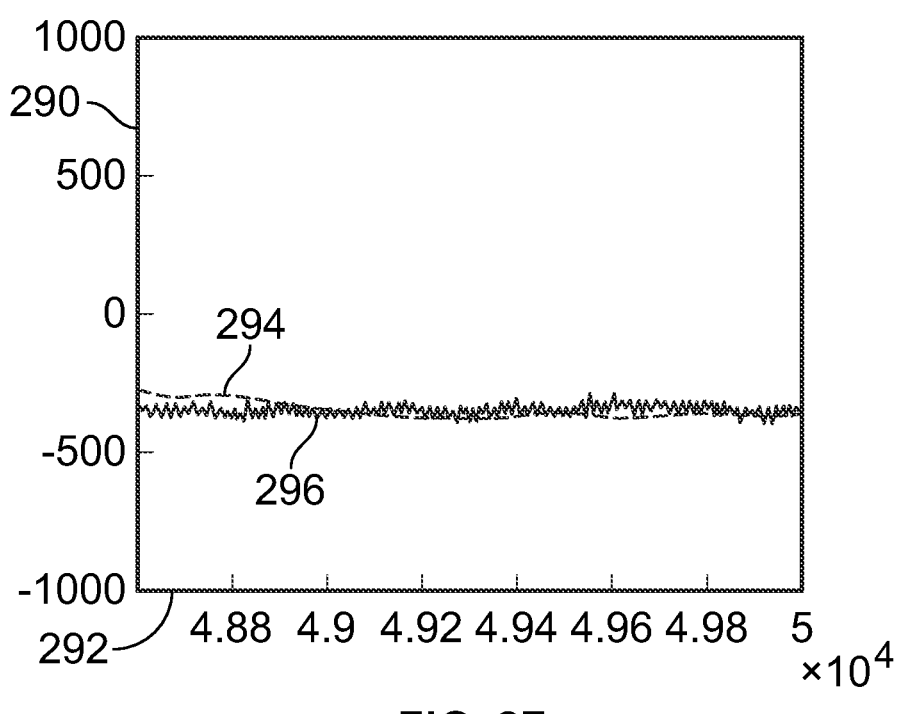
FIG. 2F illustrates a graph of position over time in accordance with embodiments herein.

In addition, or alternatively, as illustrated in FIGS. 2D-2F, posture may be monitored and recorded, including posture position 270 over time 272 for the X axis, wherein posture position over 1 second 274 along the X axis may be monitored along with posture position for 100 Hz over 1 second 276. Similarly, FIG. 2G shows posture position 280 over time 282 for the Y axis, including posture position over 1 second 284 along the Y axis along with posture position for 100 Hz over 1 second 286. Finally, for the Z axis, FIG. 2F illustrates posture position 290 over time 292, including posture position over 1 second 294 along with posture position for 100 Hz over 1 second 296.

Additionally or alternatively, in accordance with embodiments herein, the accelerometer signals and posture positions may be utilized to detect various types of erratic physical actions. Nonlimiting examples of erratic physical actions include seizures or another erratic episode experienced by the patient. For example, when a diabetic patient experiences unduly low blood sugar, the diabetic patient may experience various types of seizures. As another example, epileptic patients may experience various types of seizures or undergo other erratic physical actions. The accelerometer signals and changes in posture may be analyzed for patterns associated with such erratic physical actions, such as patterns associated with various types of seizures. For example, the erratic physical action may involve the patient falling and uncontrollably shaking while in a supine position. Another example of an erratic physical action may involve a patient standing, sitting or maintaining some other position while convulsively shaking. As yet another example, with other types of seizure related disorders, a patient may repeatedly and uncontrollably move one or more limbs in a back-and-forth motion. The erratic physical actions may be identified through accelerometer signals and posture positions. For example, templates may be developed for a patient population or for an individual patient where the templates for the X, Y and Z axes of the accelerometer signals correspond to a particular erratic physical action. Additionally or alternatively, the X, Y and Z accelerometer signals may be analyzed for other patterns known to be present during certain seizures, such as a repetitive motion in a particular direction that maintains a relatively constant frequency and/or amplitude.

While in one example the positions and activities of a patient may be obtained in an office of a physician, at a hospital, etc., in other examples, the positions and activities of the patient may be taken outside the office of the physician, at the hospital, etc. In addition, a patient may have a fit-bit, smart watch, or the like the can measure cardiac activity data while a patient is exercising. As an example, a patient may swim as a way of exercising. A hospital, physician's office, etc. is unlikely to include a swimming pool to allow determining cardiac activity data, accelerometer data, etc. while a patient swims. So, when a patient goes to swim, a monitoring system may be utilized to record cardiac activity data along with the accompanying accelerometer data associated with swimming. The monitoring device may then utilize the accelerometer data to determine a plurality of control three-dimensional point vectors related to the accelerometer data associated with swimming. In this manner, control three-dimensional point vectors can be added to the memory of the monitoring device at any time, and not just at a hospital or physicians office. The monitoring device may then use the control three-dimensional point vectors stored and related to swimming to compare to activity three-dimensional point vectors obtained at a later time.

Figure 2I:
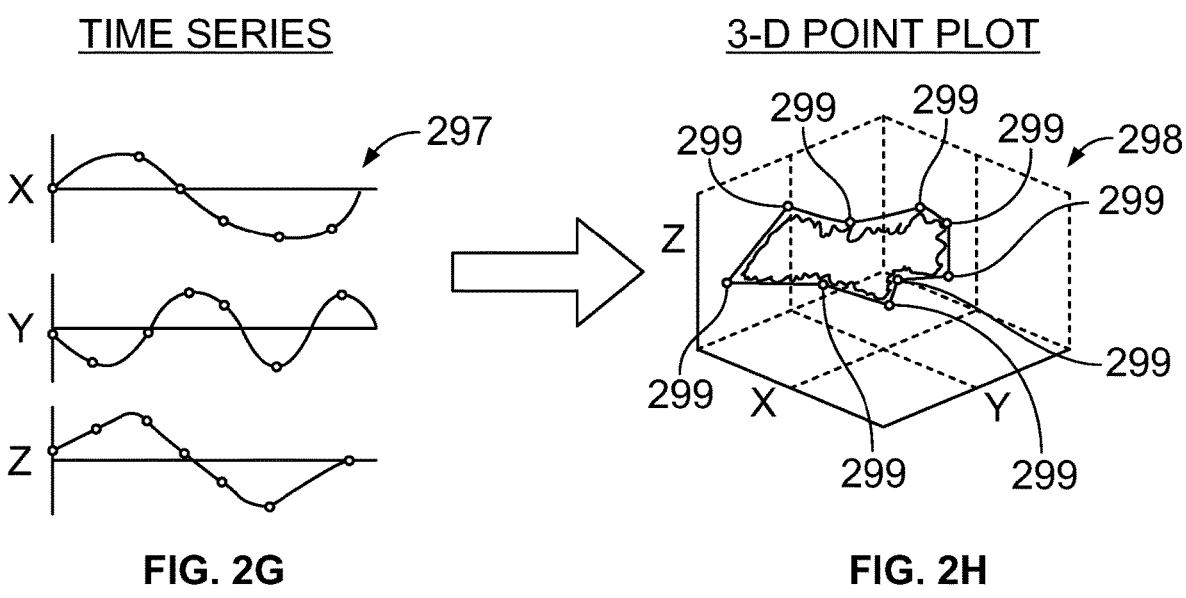
FIG. 2I illustrates a three-dimensional graph of position over time in accordance with embodiments herein.
Figure 2I:
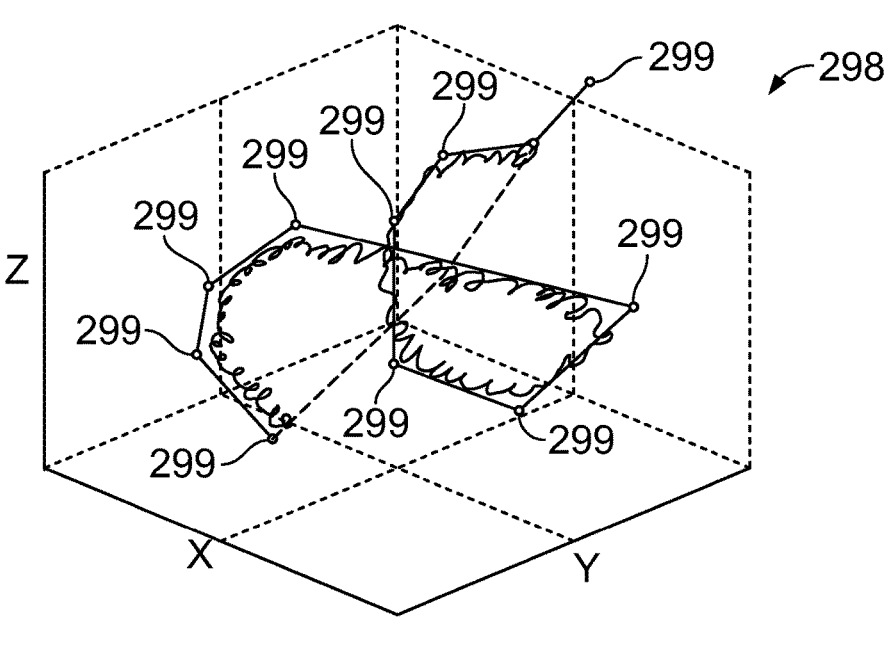

FIG. 2G illustrates an example time series graph 297 that provides the three axes when continuous accelerometer data is put on linear graphs. Compare this to FIGS. 2H and 2I that illustrate example three-dimensional point vector plots 298.

A three-dimensional point vector plot 298 may represent a shape formed from three-dimensional point vectors 299. The three-dimensional point vector plot 298 may be of control three-dimensional point vectors obtained as a template or control from accelerometer data. At a first time, such as when an IMD is implanted, the patient may perform numerous activities including walking, running, jogging, sitting, laying, or the like with each activity resulting in numerous time series data point related to the activity. Then from the time series data points the three-dimensional point vectors 299 can be determined and placed on a three-dimensional graph to form the three-dimensional point vector plots related to the activity. Because the activities and postures are repetitive in nature, the same motions are continuously detected by the accelerometer allowing for the determination of the three-dimensional point vectors utilized to represent the activity, posture, etc. of the user. When these three-dimensional point vectors are placed on a three-dimensional graph, the three-dimensional point vectors form a three-dimensional point vector plot that is a shape that may be identified. From these three-dimensional point vectors three-dimensional point vectors may be determined, identified, calculated, etc. When an activity or posture is initially provided to determine the three-dimensional point vectors for later use, the three-dimensional point vectors are control three-dimensional point vectors.

The three-dimensional point vectors may also be activity three-dimensional point vectors obtained based on activity of the user after the control three-dimensional point vectors are determined at the first time. The activity three-dimensional point vectors may then be compared to the control three-dimensional point vectors to determine the activity of a patient.

In one example, the three-dimensional point vectors 299 may be formed as piecewise linear approximations of the three-dimensional point vector plots 298 of the accelerometer data. This is in contrast to the time series graph 297 where significantly more data must be saved, taking up memory and processing space. In one example, the piecewise linear approximation can be made utilizing algorithms. In particular, each posture and activity change may be logged and a confidence score for each determined. The logs may then be consulted by a separate arrhythmia discrimination algorithm to determine whether therapy should be accelerated or delayed.

Figure 3:
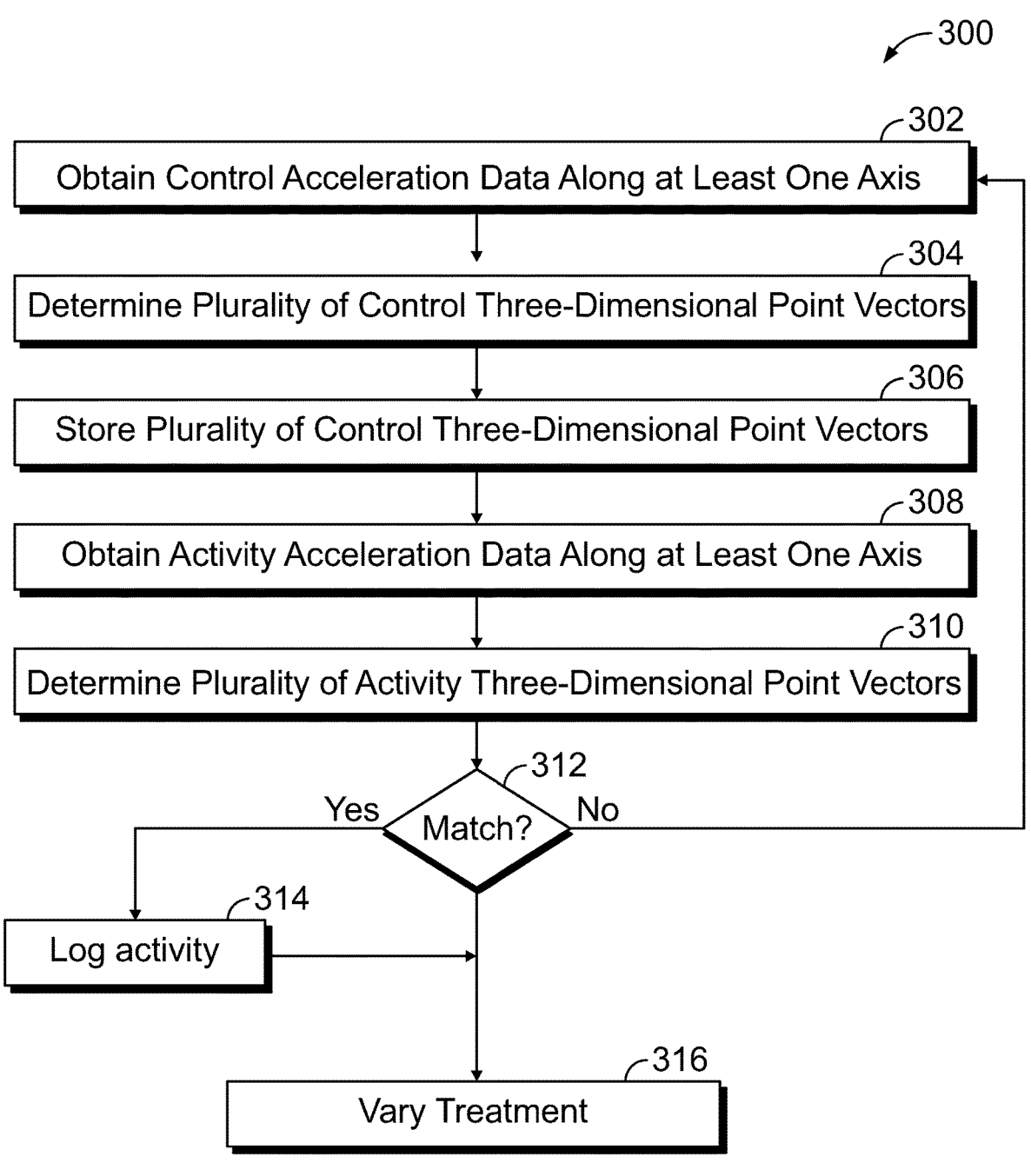
FIG. 3 illustrates a flow block diagram of a method of determining treatment for an arrythmia in accordance with embodiments herein.

FIG. 3 illustrates a flow block diagram of a method of determining treatment for an arrhythmia based on a biological signal 300. In one example, the monitoring system used to perform the method includes an accelerometer, similar to that illustrated in FIG. 1. By monitoring the physical actions of a patient, including activities and changes in position, pathologic episodes may be determined.

At 302, an accelerometer obtains control accelerometer data along at least one axis at an initial time. In an example, accelerometer data is obtained along an X-axis, Y-axis, and Z-axis. The accelerometer data may include IMD accelerometer data, activity related data, posture related data, cardiac activity data related to other data, or the like. In one example, the accelerometer data is obtained at a hospital, physician's office, or the like. Alternatively, the accelerometer data may be obtained at a remote location, including a home of a patient, swimming pool, gym, track, or the like. The IMD accelerometer data may be obtained from any of the three axes in any manner described herein. The posture related data of the accelerometer may similarly be obtained from any axis or may be a composite of the axes.

At 304, one or more processors determine a plurality of control three-dimensional point vectors related to the accelerometer data. The one or more processors receive an accelerometer data set that includes numerous three-dimensional vectors associated with a determined activity or posture of the patient. The activity or posture can include walking, jogging, swimming, sitting, standing, or the like. For each activity and/or posture, accelerometer data is continuously received during a determined time interval. In one example, the accelerometer data is obtained while a patient is walking on a treadmill. Alternatively, the accelerometer data is obtained while the patient is swimming in a pool. For most activities such as walking, jogging, swimming, etc., the motion provided is repetitive over time with similar or identical accelerometer data occurring.

Based on these accelerometer data sets the one or more processors can determine control three-dimensional point vectors where each individual control three-dimensional point vector approximates, or represents numerous sets of accelerometer data. In one example, the approximation is a piecewise linear approximation. As an example, if each of the accelerometer data sets were to be plotted on a three-dimensional graph a shape would be formed, where the individual control three-dimensional point vectors are points that if connected form that shape. In this manner, a reduced data set compared to all of the accelerometer data sets may be stored in a memory to save memory space and reduce energy used for computations related to the control three-dimensional point data.

At 306 the one or more processors store the plurality of control three-dimensional point vectors in at least one memory. Once the control three-dimensional point vectors are determined for an activity, such as walking, jogging, running, swimming, racquetball, yoga, workout, or the like the control three-dimensional point vectors are stored in the memory for later use. As a result, the one or more processors discard the accelerometer data, reducing the amount of space used in the memory.

In one example, cardiac activity data associated with the control three-dimensional point vectors is also stored in the memory. To this end, the cardiac activity data may be associated with corresponding control three-dimensional point vectors. In one example, the cardiac activity data and the corresponding control three-dimensional point vectors are stored within a lookup table.

Figure 4:
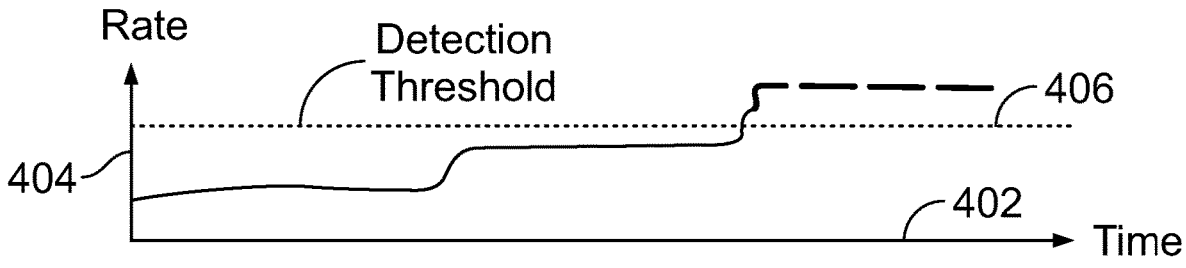
FIG. 4 illustrates a graph of heart rate over time in accordance with embodiments herein.

At 308, the one or more processors continually obtain activity accelerometer data as the patient performs activities. In one example, the one or more processors continuously obtains the accelerometer data. This includes while the patient is sitting, sleeping, exercising, walking, or the like. In another example, a threshold heart-rate is provided, and upon the heart rate of the patient being above a threshold heart-rate, the one or more processors begin continuously obtaining accelerometer data. FIG. 4 illustrates an example graph of heart rate 402 over time 404 that includes a threshold heart rate 406 for triggering obtaining accelerometer data. By providing a threshold heart-rate, the accelerometer data is not obtained during low activity times that may drain the battery of the IMD. Instead, not until the threshold heart rate is reached do the one or more processors begin obtaining the accelerometer data. In this manner, the one or more processors determine if the plurality of control three-dimensional point vectors may be required to make a diagnosis based on the biological signal.

In one example, the threshold heart-rate may be a determined heart-rate such as eighty beats per minute. In another example, the determined heart-rate is a determined amount over the average heart rate of the patient, such as twenty beats per minute over the average heart rate. In one example, the accelerometer data is obtained for a determined interval after the last occurrence of the threshold heart-rate being reached. So, in one example, every time a heart-rate of over the threshold, the accelerometer obtains accelerometer data for five minutes. In each instance, by utilizing the threshold, accelerometer data does not have to be continuously obtained, and instead, only during certain conditions is the accelerometer data obtained, saving battery life.

At 310, the one or more processors determine activity three-dimensional point vectors from the accelerometer data that is continuously obtained. As the accelerometer data is obtained, the one or more processors continuously approximate, determine, calculate, derive, etc. activity three-dimensional point vectors related to the most recent accelerometer data obtained. In this manner, each activity three-dimensional point vector is representative of numerous individual accelerometer data sets, points, readings, or the like. In one example, the approximation, determination, calculation, derivation, etc. is a piecewise linear approximation.

At 312, the one or more processors determine if the activity three-dimensional point vectors match, are similar to, correlate, etc. with control three-dimensional point vectors previously recorded and stored in the memory. As the activity three-dimensional point vectors are obtained, they may form a pattern that is similar to a pattern previously recorded as an activity by the patient. A look-up table, Euclidean distance, Manhattan distance, other comparison algorithm, or the like may be utilized to determine similarities between control three-dimensional point vectors and the activity three-dimensional point vectors. To this end, the certainty of the determination of a match may be determined. By analyzing the activity three-dimensional point vectors compared to the control three-dimensional point vectors, a physical action of patient can be determined. In one example the physical action is an activity of the patient. In another example, the physical action is a change in position of the patient. Based on the physical action, biological signals may be verified, treatments varied, or the like.

Figure 5:
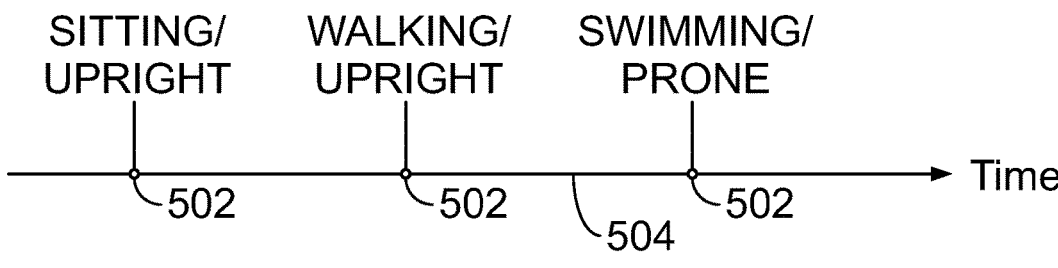
FIG. 5 illustrates a graph of a log over time in accordance with embodiments herein.

If at 312 a determination is made that the control three-dimensional point vectors and activity three-dimensional point vectors match, or are similar, optionally, at 314 the one or more processors may log the activity. For instance, if the patient goes jogging every day at the same time, the one or more processors utilize the comparison of the control three-dimensional point vectors and activity three-dimensional point vectors to log every day that jogging has occurred. A physician may then be utilized that information to see of a patient has stopped running, adjust treatments, or medication, or the like. The log provides additional information for use by the one or more processors, physician, etc. FIG. 5 illustrates a graph of an example log 500 for activities 502 provided over time 504. Alternatively, different shapes, symbols, numbers, letters, etc. may represent the activity 502. In addition, to the activity determined, the certainty of the determination may also be logged. In one example, a confidence score may be assigned to each activity. The confidence score may be based on how similar a pattern, shape, activity three-dimensional point vector match with the control three-dimensional point vectors. So, in an example when a threshold distance is utilized to determine similarity, if a determination shows the determination is right at the threshold distance, a low confidence score may be assigned to the determination. Whereas if the distances match exactly such that no distance variance is provided, the confidence score may be the highest the score can be. In this manner, the additional information is provided to the one or more processors, a physician, etc. regarding the determinations of the one or more processors, and treatment accordingly. In one example, the log, including the confidence score may be utilized by an arrhythmia discrimination algorithm to determine whether therapy should be accelerated or delayed.

After the activity is logged at 314, at 316 an arrythmia determination and/or a treatment may be varied based on the activity determined. In particular, certain activities such as walking, jogging, running, swimming, playing a game, or the like typically results in an increased heat rate. Consequently, when such activities are detected as ongoing, treatment using an IMD may be varied, altered, changed, etc. to ensure the best treatment at the best time is being provided. In addition, such activities can directly affect a determination of whether an arrythmia is present. In one example, an arrhythmia discrimination algorithm may be utilized that uses the activity along with an activity confidence score to determine if treatment or therapy should be accelerated or delayed.

If at 312, a determination is made that no match or similarity between the control three-dimensional point vectors and the activity three-dimensional point vectors the one or more processors do not vary the treatment, and instead continue the process of obtaining the accelerometer data. When the activity of the patient simply is not recognized, then treatment does not vary. For example, if the patient is playing a tennis match where there is a lot of movement, including stopping, going, running forward, backwards, side to side, etc. activity three-dimensional point vectors are determined that do not match with an existing control three-dimensional point vectors. As a result, treatment is not varied or changed.

Figure 6:
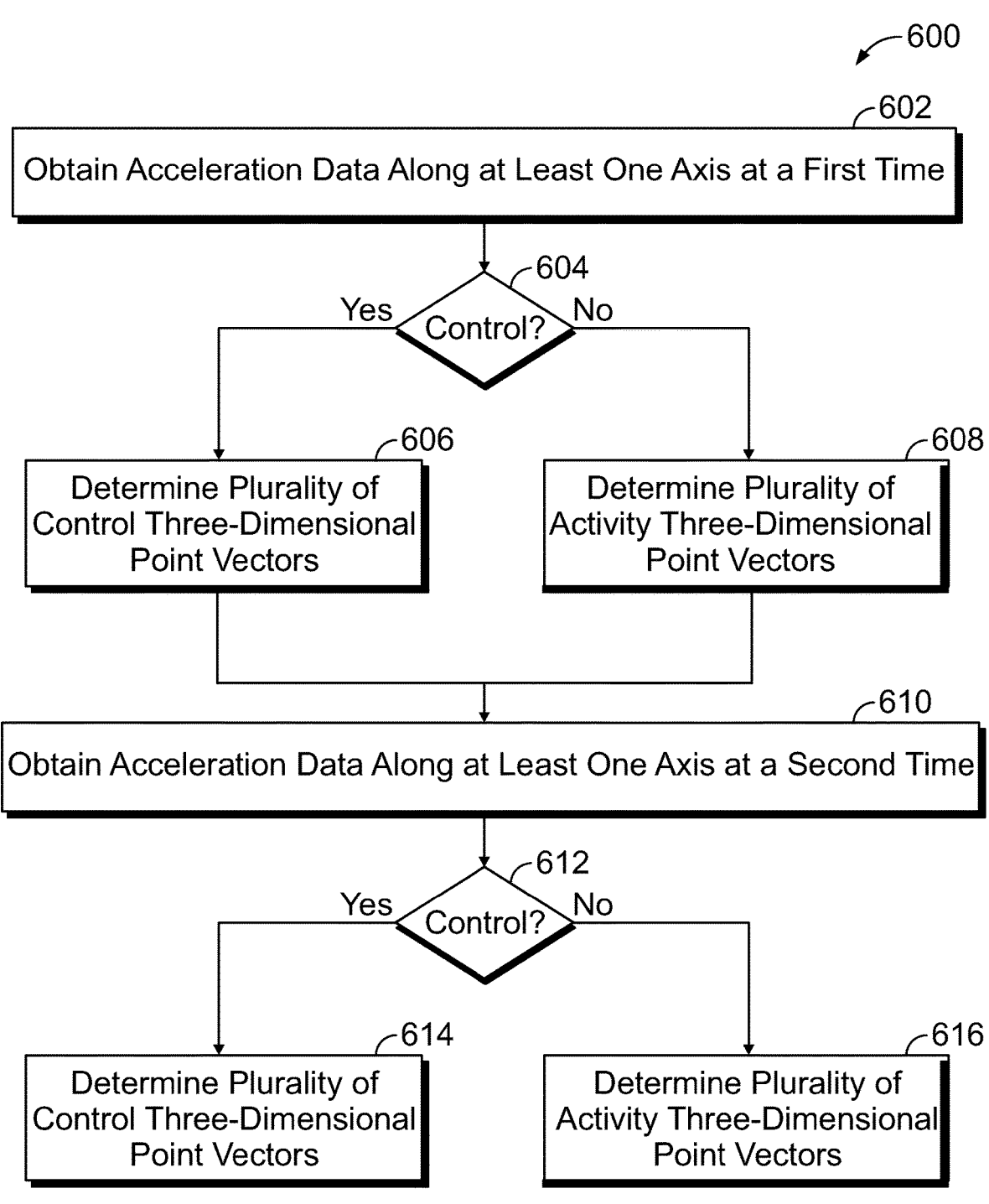
FIG. 6 illustrates a flow block diagram of a method for forming three-dimensional point vectors in accordance with embodiments herein.

FIG. 6 illustrates a method of forming three-dimensional point vectors 600. In one example the method may be performed by one or more processors and an accelerometer as provided herein.

At 602, the one or more processors obtain accelerometer data at a first time. The first time may occur in a hospital, physicians office, or the like. During the first time accelerometer data for a plurality of postures and activities may be obtained.

At 604, the one or more processors make a determination regarding whether the accelerometer data is control accelerometer data or activity accelerometer data. In one example, a physician may provide an input received by the IMD that accelerometer data is control accelerometer data. Alternatively, the patient may provide an input that accelerometer data is control accelerometer data. In yet another example, the one or more processors are configured such that all accelerometer data received by the IMD is control accelerometer data until programmed otherwise. In yet another example, determined time periods may be set, where all accelerometer data obtained during the determined time period is control accelerometer data. As an example, a physician may have a patient sit for five minutes, walk for five minutes, run for five minutes, or the like. In this manner, the five minutes is the determined time period such that all accelerometer data obtained during the five minutes is control accelerometer data. While the determined time period may be five minutes in some embodiments, in other embodiments, the determined time period may be thirty seconds, a minute, ten minutes, fifteen minutes, an hour, etc. In addition, during an initial programming, numerous determined time periods may be utilized associated with numerous postures and activities, with the accelerometer data taken in each determined time period associated with a determined posture or activity being control accelerometer data.

If at 604, the accelerometer data is considered control accelerometer data, then at 606, the one or more processors determine control three-dimensional point vectors associated with the control accelerometer data. In one example, the control accelerometer data is obtained for a determined period of time, and the activity of the patient results in a pattern related to the control accelerometer data. For example, running results in the same chest movement over and over and over again. As a result, a pattern may be formed of this movement during the determined period of time. From the numerous control three-dimensional vectors obtained, the one or more processors then may calculate, estimate, approximate, etc. plural control three-dimensional point vectors. In an example, the plural control three-dimensional point vectors are positioned such that if a straight line was drawn between the adjacent point vectors, the shape formed by all of the three-dimensional point vectors would be approximated. By utilizing three-dimensional point vectors, the acceleration data can be discarded, saving memory space.

If at 604, the accelerometer data is not considered control accelerometer data, then at 608, the one or more processors determine activity three-dimensional point vectors associated with the activity accelerometer data. If the accelerometer data is not control accelerometer data, then the accelerometer data is activity three-dimensional accelerometer data. Such activity three-dimensional accelerometer data is then converted into activity three-dimensional point vectors in a similar manner as control accelerometer data is converted into control three-dimensional point vectors.

At 610, the one or more processors obtain accelerometer data at a second time. The second time may occur outside of a hospital or physician's office setting and instead occur as a remote location such as at the patient's house, a gym, swimming pool, or the like. During the second time accelerometer data for a plurality of postures and activities may be obtained.

At 612, the one or more processors make a determination regarding whether the accelerometer data is control accelerometer data or activity accelerometer data. In one example, a patient may provide an input received by the IMD that accelerometer data is control accelerometer data. As an example, the patient may partake in a physical activity that may not be measured in a hospital or physician's office. Swimming, weightlifting, skiing, ice skating, surfing, or the like are all physical activities that may be undertaken by the patient remote of a physician's office or hospital. In such instances, the patient may input that the accelerometer data being obtained is control accelerometer data. The patient may provide the start and stop of the obtaining of the control accelerometer data manually, or by providing a determined period of time.

If at 612, the accelerometer data is control accelerometer data, then at 614 the one or more processors determine control three-dimensional point vectors. The control three-dimensional point vectors are determined as previously provided. Alternatively, if at 612 the accelerometer data is activity accelerometer data, then at 616 the one or more processors determine activity three-dimensional point vectors. These activity three-dimensional point vectors may then be compared to control three-dimensional point vectors in forming patient activity logs, making determinations related to diagnosis of an arrythmia, determinations related to medical treatments, or the like. Consequently, control accelerometer data may be obtained by a patient remote from a physician's office, hospital, care facility, etc. and may be utilized to for a comparison by later obtained activity accelerometer data.

Figure 7:
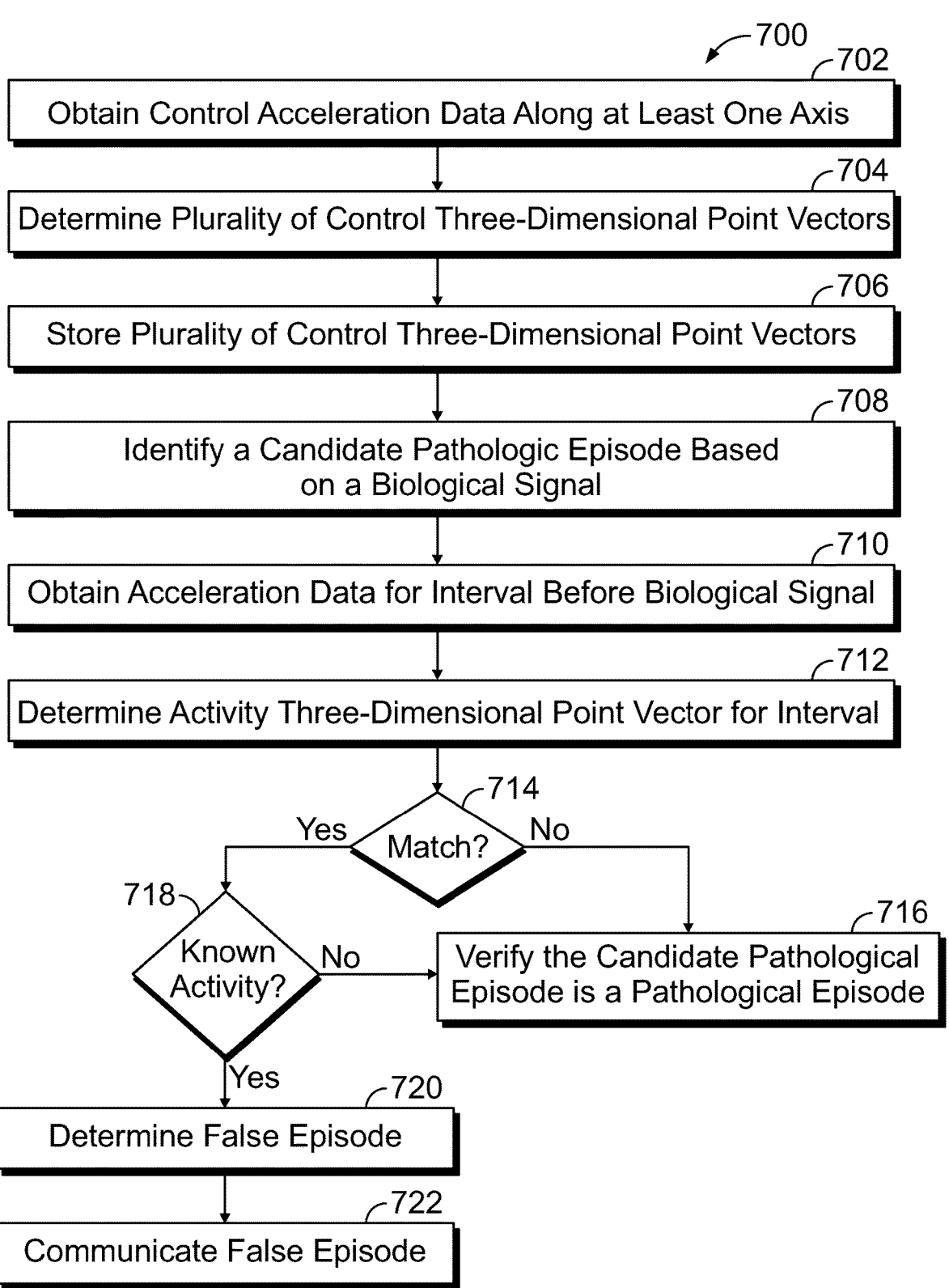
FIG. 7 illustrates a flow block diagram of a method for verifying a candidate pathological episode in accordance with embodiments herein

FIG. 7 illustrates a flow block diagram of a method 700 of verifying a candidate pathologic episode of a patient and taking remedial actions in response to verifying such a candidate pathologic episode. In one example the monitoring system used to perform the method includes an accelerometer, similar to that illustrated in FIG. 1. By monitoring the physical actions of a patient using an accelerometer, potentially adverse pathologic episodes, or conditions may be confirmed.

Non-limiting examples of candidate pathologic episodes include heart failure, stroke, syncope, arrythmia, heart attack, asystole, brady event, neurological episodes, ventricular fibrillation (VF), ventricular tachycardia (VT), a diabetic seizure, and epileptic seizure, or any other type of seizure, episodes that may result from substantial reduction or change in pulmonary arterial pressure and the like. Specifically, to reduce a false detection of a pathologic episode, such as a syncope, accelerometer data may be used to verify the detection of the pathologic episode. Alternatively, the monitoring system may be used in general to track a patient and detect a fall-episode, even without a pathologic episode occurring. In this manner, the accelerometer may serve dual purposes in both detecting falls, and confirming pathologic episodes.

At 702, an accelerometer obtains control accelerometer data along at least one axis at an initial time. The accelerometer data may include IMD accelerometer data, activity related data, posture related data, or the like. In one example, the accelerometer data is obtained at a hospital, physicians office, or the like. The IMD accelerometer data may be obtained from any of the three axes in any manner described herein. The posture related data of the accelerometer may similarly be obtained from any axis or may be a composite of the axes.

At 704, one or more processors determine a plurality of control three-dimensional point vectors related to the accelerometer data. The one or more processors receive an accelerometer data set that includes numerous three-dimensional vectors associated with a determined activity or posture of the patient. The activity or posture can include walking, jogging, swimming, sitting, standing, or the like. For each activity and/or posture, three-dimensional vectors are continuously received during a determined time interval.

For most activities such as walking, jogging, swimming, etc., the motion provided is repetitive over time with similar or identical three-dimensional vectors occurring. Then, based on these accelerometer data sets the one or more processors can determine control three-dimensional point vectors where each individual control three-dimensional point vector approximates, or represents numerous three-dimensional vectors. In one example, the approximation is a piecewise linear approximation. As an example, if each of the three-dimensional vectors were to be plotted on a three-dimensional graph (See FIGS. 2H-2I) a shape would be formed, where the individual control three-dimensional point vectors are points that if connected form that shape. In this manner, a reduced data set of the control three-dimensional point vectors may be stored in a memory instead of all of the three-dimensional vectors obtained to save memory space and reduce energy used for computations related to the control three-dimensional point vectors.

At 706 the one or more processors store the plurality of control three-dimensional point vectors in at least one memory. Once the control three-dimensional point vectors are determined for an activity, such as walking, jogging, running, swimming, racquetball, yoga, workout, or the like the control three-dimensional point vectors are stored in the memory for later use. In one example, cardiac activity data associated with the control three-dimensional point vectors is also stored in the memory. To this end, the cardiac activity data may be associated with corresponding control three-dimensional point vectors. In one example, the cardiac activity data and the corresponding control three-dimensional point vectors are stored within a lookup table.

At 708, a monitoring device operates to obtain a biological signal and identify a candidate pathologic episode based on the biological signal. In one embodiment, the monitoring device is an IMD. In one embodiment, the IMD is an ICM that monitors cardiac activity signals of the heart for arrythmias (e.g., heart attacks, VFs, VTs, syncope, etc.). The biological signal may be any signal that provides information about pathologic condition of a patient, including acceleration signals, cardiac activity signals, heart sound signals, impedance signals, pulmonary arterial pressure signals, signals indicative of a diabetic seizure, signals indicative of an epileptic seizure, or signals indicative of any other type of seizure and the like. Specifically, the biological signal may be used by a monitoring device, such as an ICM, a BGA device, PAP sensor or otherwise to detect a pathologic episode.

At 710, responsive to identifying the candidate pathologic episode, the one or more processors obtains accelerometer data for an interval associated with the candidate pathologic episode. In particular, the one or more processors determine if the plurality of three-dimensional point vectors, based on the accelerometer data obtained for the interval, are required to make a diagnosis based on the biological signal. In one example the interval is for accelerometer data received over the previous minute. In another example, the interval is for thirty seconds. In yet another example the interval is in a range between one second and five minutes. In another embodiment, the command signal may initiate the interval, and the interval may last a determined amount of time and include the time window pre/post the candidate pathologic episode.

At 712, the one or more processors determine activity three-dimensional point vectors related to the interval. By analyzing the accelerometer data, numerous accelerometer data points are obtained. In one example, the accelerometer data points may be plotted in a three-dimensional graph or plot. From the accelerometer data points, activity three-dimensional point vectors are approximated for the shape formed from accelerometer data. Similar to the control three-dimensional point vectors, estimates, or approximations are made related to the accelerometer data. In one example, one or more of the activity three-dimensional point vectors are actual accelerometer data points that were obtained. In one example, the approximation is a piecewise linear approximation. In another example, none of the activity three-dimensional point vectors are actual accelerometer data points that were obtained. In each example, the activity three-dimensional point vectors are less in number that the accelerometer data points that are obtained.

At 714, the one or more processors analyze the control three-dimensional point vectors and activity three-dimensional point vectors to identify a match, or similarity. In one example, the activity three-dimensional point vectors are compared to the control three-dimensional point vectors. In making the comparison, the plotted shapes may be compared, the three-dimensional point vectors themselves, etc. In one example, an algorithm, mathematical equation, mathematical functions, etc. may be utilized to determine whether the activity three-dimensional point vectors match or are similar to a control three-dimensional point vector. By utilizing a piecewise linear approximation instead of the complete time series using all of the accelerometer data, memory is saved. In one example, to make the comparison, a Manhattan distance can be utilized, whereas alternatively, a Euclidean distance may be utilized. Additionally or alternatively, the one or more processors may compare one or more templates, or control three-dimensional point vectors of other patients to the of the activity three-dimensional point vector of the current patient For example, three-dimensional point vectors may be developed for a patient population where the accelerometer signals correspond to a known activity. Additionally or alternatively, the activity three-dimensional point vectors may be analyzed for other patterns known to be present during certain activities, such as a repetitive motion in a particular direction that maintains a relatively constant frequency and/or amplitude.

If at 714 a determination is made that the activity three-dimensional point vectors do not match, then at 716 the one or more processes verify the candidate pathological episode is a pathological episode. In one example, to match, the comparison, or a portion of the comparison need only be within a threshold percentage. In one example, the determined distances between the control three-dimensional point vectors and the control three-dimensional point vectors are all within ten percent (10%) of one another, a match is considered presented, whereas if the distance is greater than 10%, then a match is not provided.

If at 714 a match is determined to occur, then at 718, the one or more processors determine whether the cardiac activity data resulting in the candidate pathologic episode is the same or similar to cardiac activity data related to the control three-dimensional point vectors. For example, if a patient is swimming, resulting in a sudden increase in heart rate, a false arrhythmia may be detected as the candidate pathologic episode. However, if a match is determined, that a patient is swimming, the cardiac activity data associated with the control three-dimensional point vectors may match or be similar to the cardiac activity data resulting in the candidate pathologic episode. Thus, if the cardiac activity data resulting in the candidate pathologic episode is the same or similar, a determination is made at 720 that the candidate pathologic episode is a false episode. Otherwise, if the cardiac data is not the same or similar, the candidate pathologic episode can be confirmed. In one example, the cardiac activity data may be considered the same or similar based on a comparison and being within a threshold amount. An algorithm, mathematical function, equation, etc. may be utilized to make the determination. In one example, a lookup table may be utilized to make the determination. So, by determining the physical action of the patient utilizing the accelerometer data, a false episode may be detected. In example embodiments, the physical action can be an activity of the patient, a change in position of the patient, or the like.

A false episode represents a candidate pathologic episode that was incorrectly detected or determined by a monitoring device. In contrast, an actual episode is provided with the candidate pathologic episode detected by a monitoring device is correct. In an example, in response to denying the candidate pathologic episode as a false episode, the IMD may communicate a "false positive" signal to a remote device or third party, wherein the false positive signal indicates that the IMD has incorrectly identified a candidate pathologic episode. Additionally, the false positive signal may be logged in a storage device or memory to track trends or otherwise monitor for a potentially faulty or malfunctioning monitoring device.

Additionally or alternatively, at 722, the one or more processors may deny the candidate pathologic episode as a false episode, and provide a communication to a remote device that an episode is a false episode. The one or more processors may further communicate additional information related to the posture and/or activity three-dimensional point vectors, such as the raw acceleration signals or an indication of one or more characteristics within the acceleration signals. In such a case, an automated system or a physician remote to the patient could make determinations related to the health of the patient.

Figure 8:
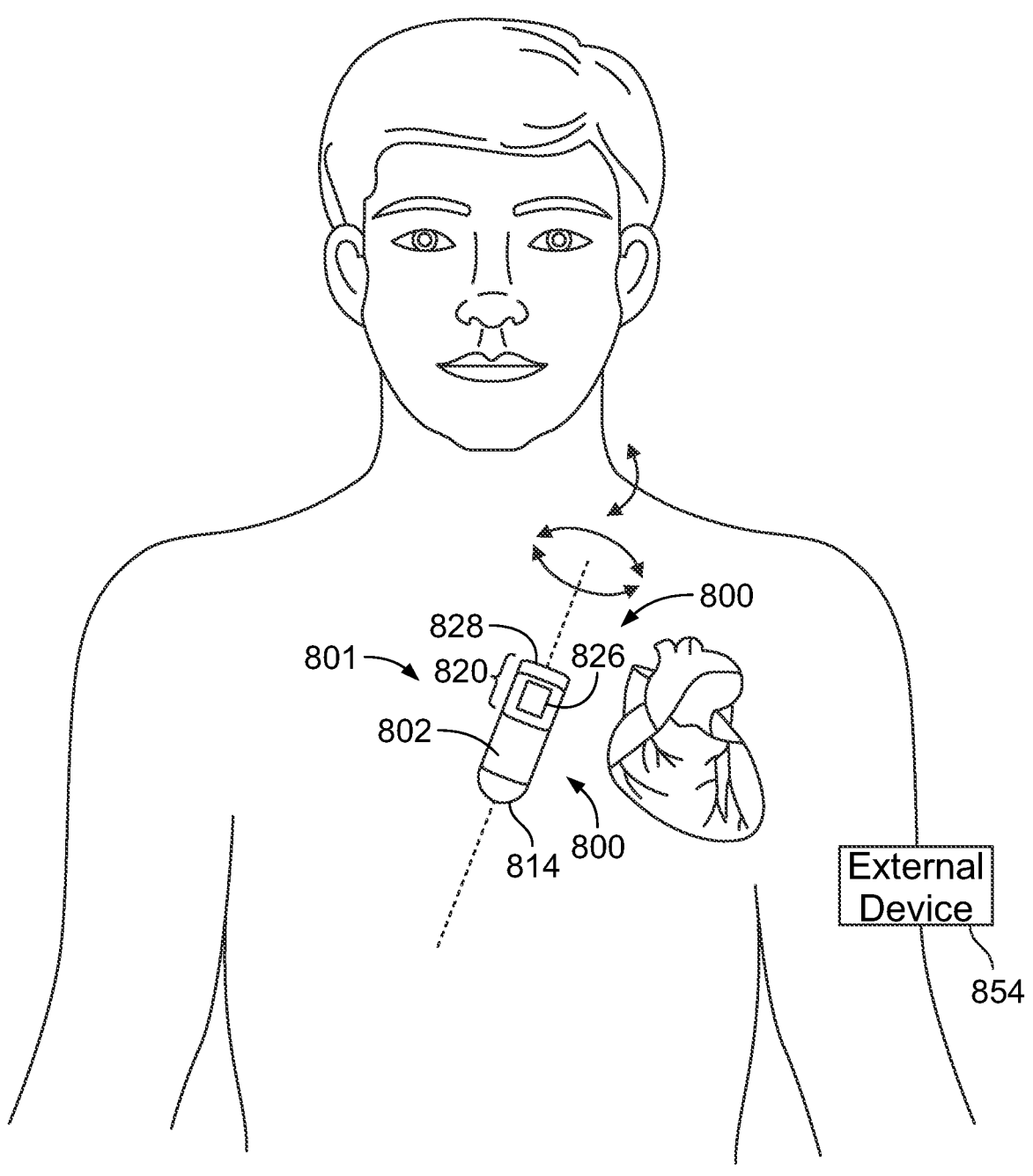
FIG. 8 illustrates an implantable cardiac monitoring device (ICM) intended for subcutaneous implantation at a site near the heart in accordance with embodiments herein.

FIG. 8 illustrates an example monitoring device 800 that is an IMD intended for subcutaneous implantation at a site near the heart that may house a monitoring system 801. In one example the monitoring system 801 is the monitoring system described in FIG. 1. The monitoring device 800 is illustrated as exemplary only, and the monitoring system 801 may be included in other systems. The monitoring device 800 includes two or more spaced-apart sense electrodes 814, 826 positioned with respect to a housing 802. The sense electrodes 814, 826 provide for detection of far field electrogram signals. The header 820 includes an antenna 828 and the electrode 826. The antenna 828 is configured to wirelessly communicate with an external device 854 in accordance with one or more predetermined wireless protocols (e.g., Bluetooth, Bluetooth low energy, Wi-Fi, etc.).

The housing 802 includes various other components such as: sense electronics for receiving signals from the electrodes, a microprocessor for analyzing the far field CA signals, including assessing the presence of R-waves in cardiac beats occurring while the monitoring device is in different locations relative to gravitational force, a loop memory for temporary storage of CA data, a device memory for long-term storage of CA data, sensors for detecting activity of the patient, including an accelerometer for detecting acceleration signatures indicative of heart sound, and a battery for powering components.

The monitoring device 800 may sense far field, subcutaneous CA signals, processes the CA signals to detect arrhythmias and if an arrhythmia is detected, automatically records the CA signals in memory for subsequent transmission to an external device 854.

The monitoring device 800 is implanted in a position and orientation such that, when the patient stands, the monitoring device 800 is located at a reference position and orientation with respect to a global coordinate system that is defined relative to a gravitational direction. For example, the gravitational direction may be along the Z-axis while the X-axis is between the left and right arms.

Figure 9:
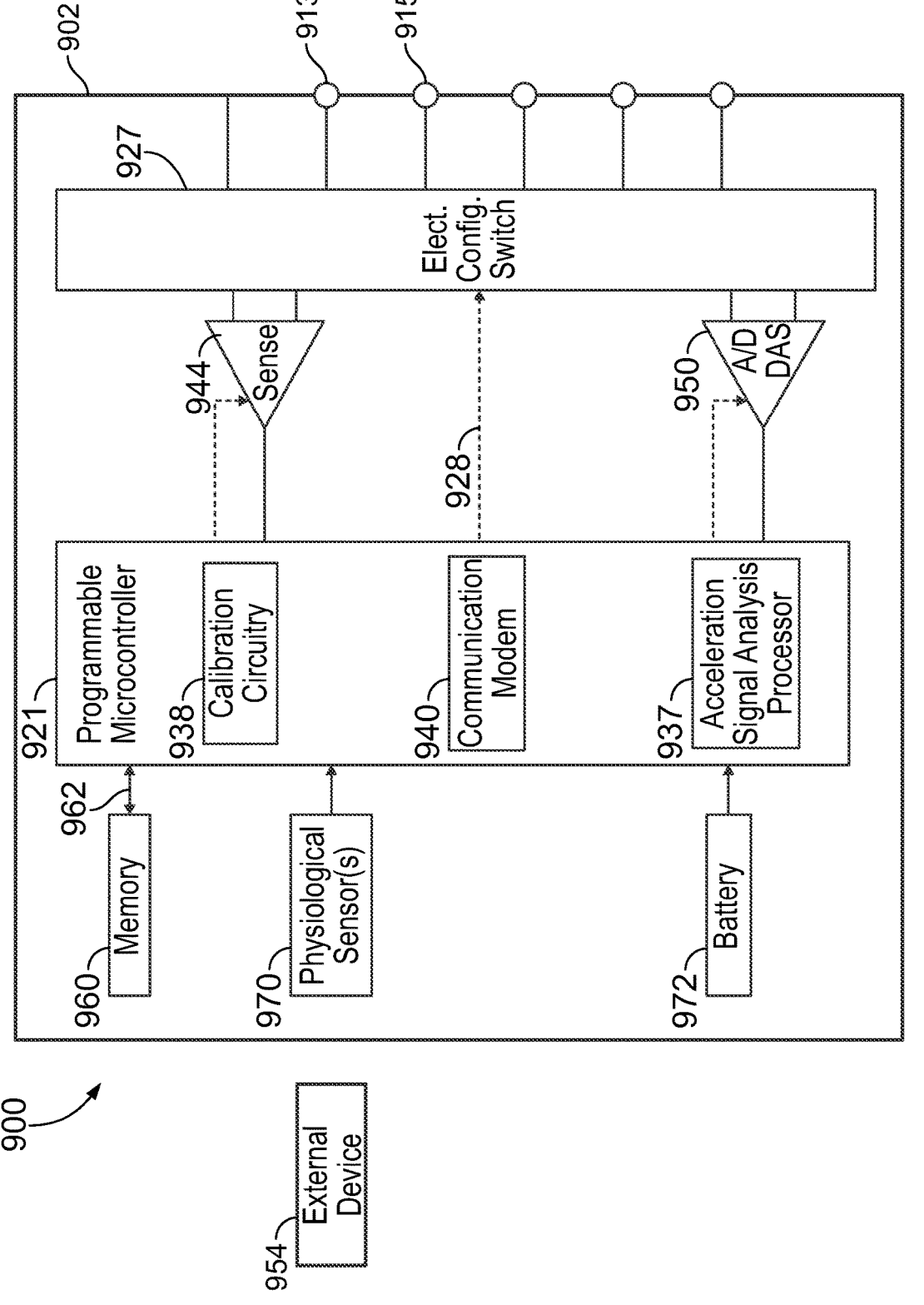
FIG. 9 illustrates a block diagram of the ICM formed in accordance with embodiments herein.

FIG. 9 shows a block diagram of a monitoring device 900 formed in accordance with embodiments herein. The monitoring device 900 has a housing 902 to hold the electronic/computing components. The housing 902 (which is often referred to as the "can," "case," "encasing," or "case electrode") may be programmably selected to act as an electrode for certain sensing modes. Housing 902 further includes a connector (not shown) with at least one terminal 913 and optionally additional terminals 915. The terminals 913, 915 may be coupled to sensing electrodes that are provided upon or immediately adjacent the housing 902. Optionally, more than two terminals 913, 915 may be provided in order to support more than two sensing electrodes, such as for a bipolar sensing scheme that uses the housing 902 as a reference electrode. Additionally or alternatively, the terminals 913, 915 may be connected to one or more leads having one or more electrodes provided thereon, where the electrodes are located in various locations about the heart. The type and location of each electrode may vary.

A switch 927 is optionally provided to allow selection of different electrode configurations under the control of the microcontroller 921. The electrode configuration switch 927 may include multiple switches for connecting the desired electrodes to the appropriate I/O circuits, thereby facilitating electrode programmability. The switch 927 is controlled by a control signal 928 from the microcontroller 921. Optionally, the switch 927 may be omitted and the I/O circuits directly connected via terminals 913, 915.

The monitoring device 900 includes sensing circuit 944 selectively coupled to one or more electrodes that perform sensing operations, through the switch 927 to detect cardiac activity data indicative of cardiac activity. Optionally, the sensing circuit 944 may be removed entirely, and the microcontroller 921 perform the operations described herein based upon the CA signals from the A/D data acquisition system 950 directly coupled to the electrodes. The output of the sensing circuit 944 is connected to the microcontroller 921 which, in turn, determines when to store the cardiac activity data of CA signals (digitized by the A/D data acquisition system 950) in the memory 960.

The monitoring device 900 includes a programmable microcontroller 921 that controls various operations of the monitoring device 900, including cardiac monitoring. Microcontroller 921 includes a microprocessor (or equivalent control circuitry), RAM and/or ROM memory, logic and timing circuitry, state machine circuitry, and I/O circuitry. The microcontroller 921 is configured to implement the operations described herein in connection with collecting and analyzing accelerometer signals.

The microcontroller 921 may also include calibration circuitry 938 that is configured to implement the calibration operations described herein. Among other things, the calibration circuitry 938 obtains baseline accelerometer signals from an accelerometer 970 in connection with specific patient postures. The postures may include supine, standing, laying on a right side, laying on are left side, angled, or the like. The calibration circuitry 938 may also calculate synthetic baseline accelerometer signals based on orthogonal baseline accelerometer signals that are directly measured by the accelerometer 970 as described herein. Although not shown, the microcontroller 921 may further include other dedicated circuitry and/or firmware/software components that assist in monitoring various conditions of the patient's heart and managing pacing therapies.

The monitoring device 900 is further equipped with a communication modem (modulator/demodulator) 940 to enable wireless communication. In one implementation, the communication modem 940 uses high frequency modulation, for example using RF, Bluetooth, or Bluetooth Low Energy telemetry protocols. The signals are transmitted in a high frequency range and will travel through the body tissue in fluids without stimulating the heart or being felt by the patient. The communication modem 940 may be implemented in hardware as part of the microcontroller 921, or as software/firmware instructions programmed into and executed by the microcontroller 921. Alternatively, the modem 940 may reside separately from the microcontroller as a standalone component, or external device 954. The modem 940 facilitates data retrieval from a remote monitoring network. The modem 940 enables timely and accurate data transfer directly from the patient to an electronic device utilized by a physician.

By way of example, the external device 954 may represent a bedside monitor installed in a patient's home and utilized to communicate with the monitoring device 900 while the patient is at home, in bed or asleep. The external device 954 may be a programmer used in the clinic to interrogate the monitoring device 900, retrieve data and program detection criteria and other features. The external device 954 may be a PDE (e.g., smartphone, tablet device, laptop computer, smartwatch, and the like) that can be coupled over a network (e.g., the Internet) to a remote monitoring service, medical network and the like. The external device 954 facilitates access by physicians to patient data as well as permitting the physician to review real-time accelerometer data sets as collected by the monitoring device 900.

The microcontroller 921 is coupled to a memory 960 by a suitable data/address bus 962. The memory 960 stores the accelerometer signals, accelerometer data sets, reference posture related data sets, cardiac activity signals, as well as the markers and other data content associated with detection and determination of the condition of the heart of the patient.

The monitoring device 900 can further include one or more accelerometer circuits 937. For example, the accelerometer circuits 937 may be part of a monitoring device 900, or may represent one or more accelerometers, such as a three-dimensional (3D) accelerometer. The accelerometer circuits 937 may utilize a piezoelectric, a piezoresistive, and/or capacitive components are commonly used to convert the mechanical motion of the 3D accelerometer into an electrical signal received by the microcontroller 921. By way of example, the 3-D accelerometer may three outputs/channels that generate three corresponding electrical signals indicative of motion in three corresponding directions, namely X, Y and Z directions. The electrical signals associated with each of the three directional components may be divided into different frequency components to obtain different types of information therefrom.

The accelerometer circuits 937 may be utilized to execute instructions from the microcontroller 921, including determining three-dimensional point vectors from accelerometer data sets. The three-dimensional point vectors can include control three-dimensional point vectors and activity three-dimensional point vectors.

The accelerometer circuits 937 collect device location information with respect to gravitational force while the monitoring device 900 collects cardiac activity signals in connection with multiple cardiac beats. In one example, the accelerometer circuits 937 include the accelerometer as described in relation to FIG. 1. The microcontroller 921 may utilize the signals from the accelerometer circuits 937. While shown as being included within the housing 902, the accelerometer circuit 970 may be external to the housing 902, yet still, be implanted within or carried by the patient.

A battery 972 provide operating power to all of the components in the monitoring device 900. The battery 972 is capable of operating at low current drains for long periods of time. The battery 972 also desirably has a predictable discharge characteristic so that elective replacement time can be detected.

Figure 10:
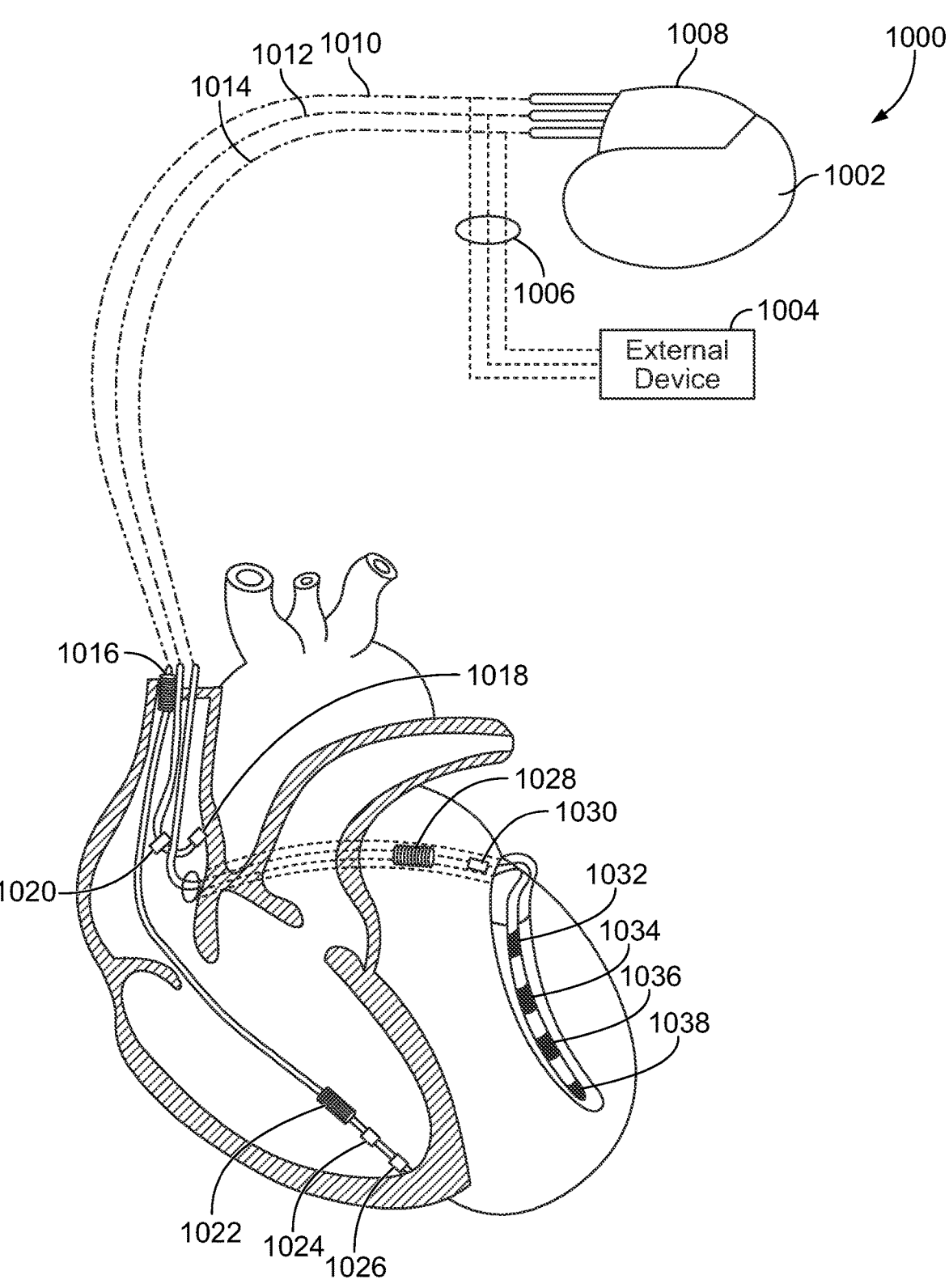
FIG. 10 illustrates an implantable medical device (IMD) intended for subcutaneous implantation at a site near the heart in accordance with embodiments herein.

FIG. 10 illustrates an alternative monitoring device 1000 that may apply treatment, such as a shock when a candidate pathologic episode such as VF or VT is verified using the method of FIG. 5. The monitoring device 1000 may be a dual-chamber stimulation device capable of treating both fast and slow arrhythmias with stimulation therapy, including cardioversion, defibrillation, anti-tachycardia pacing and pacing stimulation, as well as capable of detecting heart failure, evaluating its severity, tracking the progression thereof, and controlling the delivery of therapy and warnings in response thereto. The monitoring device 1000 may be controlled to sense atrial and ventricular waveforms of interest, discriminate between two or more ventricular waveforms of interest, deliver stimulus pulses or shocks, and inhibit application of a stimulation pulse to a heart based on the discrimination between the waveforms of interest and the like. Exemplary structures for the monitoring device 1000 are discussed and illustrated in the drawings herewith.

The monitoring device 1000 includes a housing 1002 that is joined to a header assembly 1008 that holds receptacle connectors connected to a right ventricular lead 1010, a right atrial lead 1012, and a coronary sinus lead 1014, respectively. The leads 1012, 1014 and 1010 measure cardiac signals of the heart. The right atrial lead 1012 includes an atrial tip electrode 1018 and an atrial ring electrode 1020. The coronary sinus lead 1014 includes a left atrial ring electrode 1028, a left atrial coil electrode 1030 and one or more left ventricular electrodes 1032-1038 (e.g., also referred to as P1, M1, M2 and D1) to form a multi-pole LV electrode combination. The right ventricular lead 1010 includes an RV tip electrode 1026, an RV ring electrode 1024, an RV coil electrode 1022, and an SVC coil electrode 1016. The leads 1012, 1014 and 1010 detect IEGM signals that are processed and analyzed as described herein. The leads 1012, 1014 and 1010 also delivery therapies as described herein.

During implantation, an external device 1004 is connected to one or more of the leads 1012, 1014 and 1010 through temporary inputs 1006. The inputs 1006 of the external device 1004 receive IEGM signals from the leads 1012, 1014 and 1010 during implantation and display the IEGM signals to the physician on a display. Hence, the external device 1004 receives the IEGM cardiac signals through telemetry circuit inputs. The physician or another user controls operation of the external device 1004 through a user interface.

Figure 11:
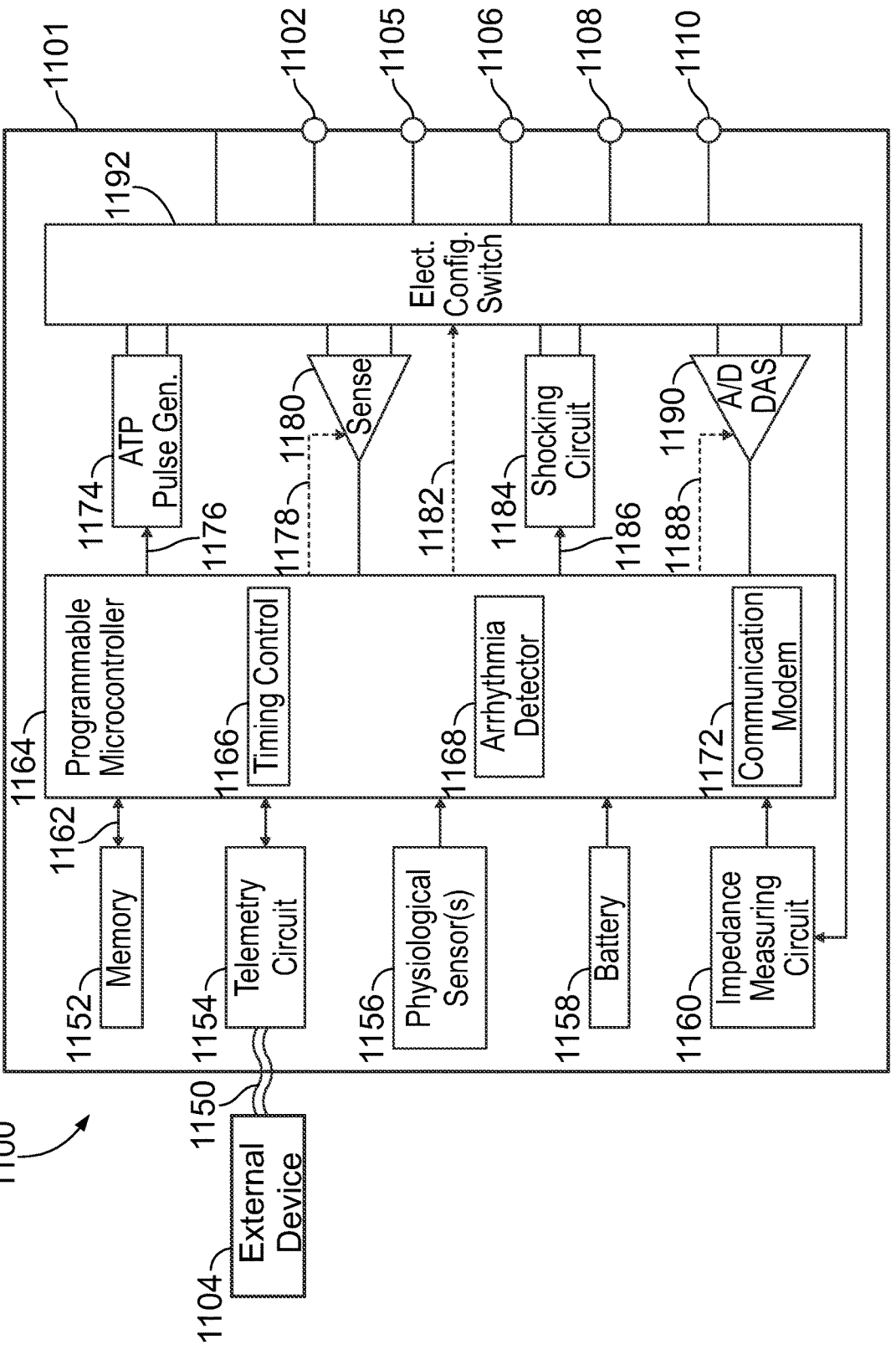
FIG. 11 illustrates a block diagram of the IMD formed in accordance with embodiments herein.

FIG. 11 illustrates an example block diagram of a monitoring device 1100 that is implanted into the patient as part of the implantable cardiac system. In one example, the monitoring device 1100 is an IMD. The monitoring device 1100 may be implemented as a full-function biventricular pacemaker, equipped with both atrial and ventricular sensing and pacing circuitry for four chamber sensing and stimulation therapy (including both pacing and shock treatment). Optionally, the monitoring device 1100 may provide full-function cardiac resynchronization therapy. Alternatively, the monitoring device 1100 may be implemented with a reduced set of functions and components. For instance, the monitoring device may be implemented without ventricular sensing and pacing.

The monitoring device 1100 has a housing 1101 to hold the electronic/computing components. The housing 1101 (which is often referred to as the "can", "case", "encasing", or "case electrode") may be programmably selected to act as the return electrode for certain stimulus modes. Housing 1101 further includes a connector (not shown) with a plurality of terminals 1102, 1105, 1106, 1108, and 1110. The type and location of each electrode may vary. For example, the electrodes may include various combinations of ring, tip, coil and shocking electrodes and the like.

The monitoring device 1100 includes a programmable microcontroller 1164 that controls various operations of the monitoring device 1100. Microcontroller 1164 includes a microprocessor (or equivalent control circuitry), RAM and/or ROM memory, logic and timing circuitry, state machine circuitry, and I/O circuitry. The monitoring device 1100 further includes a first chamber pulse generator 1174 that generates stimulation pulses for delivery by one or more electrodes coupled thereto. The pulse generator 1174 is controlled by the microcontroller 1164 via control signal 1176. The pulse generator 1174 is coupled to the select electrode(s) via an electrode configuration switch 1192, which includes multiple switches for connecting the desired electrodes to the appropriate I/O circuits, thereby facilitating electrode programmability. The switch 1192 is controlled by a control signal 1186 from the microcontroller 1164.

Microcontroller 1164 is illustrated to include timing control circuitry 1166 to control the timing of the stimulation pulses (e.g., pacing rate, atrio-ventricular (AV) delay, atrial interconduction (A-A) delay, or ventricular interconduction (V-V) delay, etc.). Microcontroller 1164 also has an arrhythmia detector 1168 for detecting arrhythmia conditions. Although not shown, the microcontroller 1164 may further include other dedicated circuitry and/or firmware/software components that assist in monitoring various conditions of the patient's heart and managing pacing therapies.

The monitoring device 1100 is further equipped with a communication modem (modulator/demodulator) 1172 to enable wireless communication with other devices, implanted devices, and/or external devices. The monitoring device 1100 includes sensing circuitry 1180 selectively coupled to one or more electrodes that perform sensing operations, through the switch 1192, to detect the presence of cardiac activity.

The output of the sensing circuitry 1180 is connected to the microcontroller 1164 which, in turn, triggers or inhibits the pulse generator 1174 in response to the absence or presence of cardiac activity. The sensing circuitry 1180 receives a control signal 1178 from the microcontroller 1164 for purposes of controlling the gain, threshold, polarization charge removal circuitry (not shown), and the timing of any blocking circuitry (not shown) coupled to the inputs of the sensing circuitry.

In the example of FIG. 11, a single sensing circuit 1180 is illustrated. Optionally, the monitoring device 1100 may include multiple sensing circuit, similar to sensing circuit 1180, where each sensing circuit is coupled to one or more electrodes and controlled by the microcontroller 1164 to sense electrical activity detected at the corresponding one or more electrodes. The sensing circuit 1180 may operate in a unipolar sensing configuration or in a bipolar sensing configuration.

The monitoring device 1100 further includes an analog-to-digital (A/D) data acquisition system (DAS) 1190 coupled to one or more electrodes via the switch 1192 to sample cardiac signals across any pair of desired electrodes. The microcontroller 1164 is also coupled to a memory 1152 by a suitable data/address bus 1162. The programmable operating parameters used by the microcontroller 1164 are stored in memory 1152 and used to customize the operation of the monitoring device 1100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The telemetry circuit 1154 allows intracardiac electrograms and status information relating to the operation of the monitoring device 1100 (as contained in the microcontroller 1164 or memory 1152) to be sent to the external device 1104 through the established communication link 1150.

The monitoring device 1100 can further include one or more physiologic sensors 1156. Such sensors are commonly referred to as "rate-responsive" sensors because they are typically used to adjust pacing stimulation rates according to the exercise state of the patient. However, the physiological sensor 1156 may further be used to detect changes in cardiac output, changes in the physiological condition of the heart, or diurnal changes in activity (e.g., detecting sleep and wake states).

A battery 1158 provides operating power to all of the components in the monitoring device 1100. The monitoring device 1100 further includes an impedance measuring circuit 1160, which can be used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. The impedance measuring circuit 1160 is coupled to the switch 1192 so that any desired electrode may be used. The monitoring device 1100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 1164 further controls a shocking circuit 1184 by way of a control signal 1186.

Figure 12:
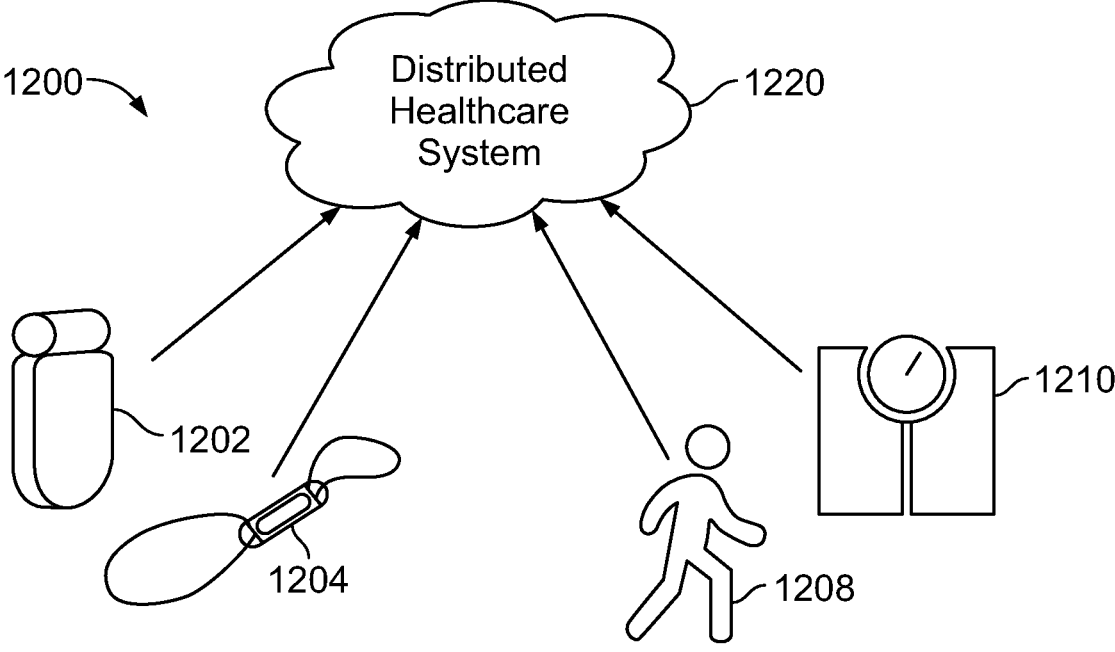
FIG. 12 illustrates a schematic diagram of a healthcare system in accordance with embodiments herein.

FIG. 12 illustrates a digital healthcare system implemented in accordance with embodiments herein. The system integrates accelerometer signals and the other information derived from accelerometer signals with other health data in connection with monitor a patient condition, progression of a health condition, trends in a patient's health condition, treatment, changes in therapy/medication and the like. The healthcare systems may include wearable PDE that communicate with an IMD or accelerometer and a remote database. As a result, the healthcare system may monitor health parameters of patient, including MD accelerometer data and TR parameters, and provide a diagnosis for the patient based on the monitored health parameters.

The system may be implemented with various architectures, that are collectively referred to as a healthcare system 1220. By way of example, the healthcare system 1220 may be implemented as described herein. The healthcare system 1220 is configured to receive data from a variety of external and implantable sources including, but not limited to, active IMDs 1202 capable of delivering therapy to a patient, passive IMDs or sensors 1204, wearable sensors 1208, and point-of-care (POC) devices 1210 (e.g., at home or at a medical facility). Any of the IMD 1202, sensor 1204, and/or sensor 1208 may implement an accelerometer circuitry and perform the analysis of accelerometer signals as described herein. The data from one or more of the external and/or implantable sources is collected and communicated to one or more secure databases within the healthcare system 1220. Optionally, the patient and/or other users may utilize a PDE device, such as a smart phone, tablet device, etc., to enter data. For example, a patient may use a smart phone to provide feedback concerning activities performed by the patient, a patient diet, nutritional supplements and/or medications taken by the patient, how a patient is feeling (e.g., tired, dizzy, weak, good), etc.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method, or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD- ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices, and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:
1. A system for verifying a candidate pathologic episode of a patient, the system comprising:
an accelerometer configured to be implanted in the patient, the accelerometer configured to obtain accelerometer data along at least one axis;
memory configured to store program instructions;
one or more processors that, when executing the program instructions, are configured to:
obtain accelerometer data;
determine a plurality of three-dimensional (3D) point vectors related to the accelerometer data;
obtain a biological signal and identify a candidate pathologic episode based on the biological signal;
analyze the plurality of three-dimensional point vectors to identify a physical action experienced by the patient; and
verify the candidate pathologic episode based on the physical action.
2. The system of claim 1, wherein to determine the plurality of three-dimensional point vectors comprises analyzing the accelerometer data, and approximating the plurality of three-dimensional point vectors related to movement by the patient in a global coordinate system.

3. The system of claim 2, wherein the one or more processors are further configured to store the plurality of three-dimensional point vectors in the memory and discard the accelerometer data.

4. The system of claim 2, wherein the one or more processors are further configured to store the candidate pathologic episode in the memory as an actual episode or a false episode based on the physical action analyzed.

5. The system of claim 1, wherein the one or more processors are further configured to determine if the plurality of three-dimensional point vectors are required to make a diagnosis based on the biological signal.

6. The system of claim 1, wherein the physical action is activity of the patient or change in position of the patient.

7. The system of claim 1, wherein the one or more processors are further configured to deny the candidate pathologic episode as a false episode when the physical action does not correspond to the candidate pathologic episode.

8. The system of claim 1, wherein the biological signal corresponds to a cardiac activity signal, and the candidate pathologic episode is at least one of a heart failure, stroke, syncope, arrythmia, heart attack, brady event, asystole, ventricular fibrillation, ventricular tachycardia, or seizure.

9. The system of claim 1, wherein responsive to identifying the candidate pathologic episode, the one or more processors are configured to:

obtain accelerometer data for an interval associated with the candidate pathologic episode;

determine a plurality of activity three-dimensional point vectors; and compare the plurality of activity three-dimensional point vectors with a plurality of three-dimensional point vectors.

10. The system of claim 9, wherein analyzing the plurality of three-dimensional point vectors to identify the physical action experienced by the patient includes comparing the plurality of activity three-dimensional point vectors with the plurality of control three-dimensional point vectors.

11. The systema of claim 1, wherein the accelerometer is configured to obtain accelerometer data along at least two axes, the plurality of 3D point vectors are indicative of movement of the patient over time relative to the at least two axes, and the analysis identifies the physical action, within the movement, experienced by the patient over the time.

12. The system of claim 1, wherein the plural 3D point vectors form a shape that approximates the movement of the patient over time with respect to at least two of an X-coordinate, Y-coordinate, and Z-coordinate in a coordinate system.

13. The system of claim 1, wherein the plural 3D point vectors form a shape that approximates the movement of the patient over time within a coordinate system.

14. A computer implemented method for verifying a candidate pathologic episode of a patient, the method comprising:

obtaining accelerometer data;

determining a plurality of three-dimensional (3D) point vectors related to the accelerometer data;

obtaining a biological signal and identify a candidate pathologic episode based on the biological signal;

analyzing the plurality of three-dimensional point vectors to identify a physical action experienced by the patient; and verifying the candidate pathologic episode based on the physical action.

15. The computer implemented method of claim 14, wherein determining the plurality of control three-dimensional point vectors comprises analyzing the accelerometer data, and approximating the plurality of control three-dimensional point vectors related to movement by the patient in a global coordinate system.

16. The computer implemented method of claim 15, further comprising storing the plurality of control three-dimensional point vectors in the memory and discarding the accelerometer data.

17. The computer implemented method of claim 15, further comprising storing the candidate pathologic episode in the memory as an actual episode or a false episode based on the physical action analyzed.

18. The computer implemented method of claim 14, further comprising determining if the plurality of control three-dimensional point vectors are required to make a diagnosis based on the biological signal.

19. The computer implemented method of claim 14, wherein the accelerometer is configured to obtain accelerometer data along at least two axes, the plurality of 3D point vectors are indicative of movement of the patient over time relative to the at least two axes, and the analysis identifies the physical action, within the movement, experienced by the patient over the time.

20. A system for verifying a candidate pathologic episode of a patient, the system comprising:

an accelerometer configured to be implanted in the patient, the accelerometer configured to obtain accelerometer data along at least one axis;

memory configured to store program instructions;

one or more processors that, when executing the program instructions, are configured to:

obtain first accelerometer data;

determine a plurality of control three-dimensional point vectors related to the first accelerometer data;

obtain a biological signal and identify a candidate pathologic episode based on the biological signal;

responsive to identifying the candidate pathologic episode, obtain second accelerometer data for an interval associated with the candidate pathologic episode;

determine a plurality of activity three-dimensional point vectors related to the second accelerometer data obtained over the interval associated with the candidate pathologic episode;

compare the activity three-dimensional point vectors to the control three-dimensional point vectors; and verify the candidate pathologic episode based on the comparison between the activity three-dimensional point vectors and the control three-dimensional point vectors.

21. The system of claim 20, wherein to determine the plurality of control three-dimensional point vectors comprises analyzing the accelerometer data, and approximating the plurality of control three-dimensional point vectors related to the accelerometer data.

22. The system of claim 21, wherein the one or more processors are further configured to store the plurality of control three-dimensional point vectors in the memory and discard the accelerometer data.

23. The system of claim 20, wherein the one or more processors are further configured to store the candidate pathologic episode in the memory as an actual episode or a false episode based on the comparison between the activity three-dimensional point vectors and the control three-dimensional point vectors.

24. The system of claim 20, wherein the one or more processors are further configured to determine if the plurality of control three-dimensional point vectors are required to make a diagnosis based on the biological signal.

25. The system of claim 20, wherein the plurality of control and activity 3D point vectors are indicative of movement of the patient over time relative to the at least one axis.

\* \* \* \* \*